US008580854B2

(12) United States Patent (10) Patent No.: US 8,580,854 B2
Rahbar et al. (45) Date of Patent: Nov. 12, 2013

(54) METHODS OF SUPPRESSION OF RAGE GENE EXPRESSION AND RAGE TRIGGERED INFLAMMATORY GENES BY SELECTED AGE-INHIBITORS

(75) Inventors: Samuel Rahbar, Beverly Hills, CA (US); Rama Natarajan, Hacienda Heights, CA (US)

(73) Assignee: City of Hope, Duarte, CA (US)

( * ) Notice: Subject to any disclaimer, the term of this patent is extended or adjusted under 35 U.S.C. 154(b) by 1496 days.

(21) Appl. No.: 11/594,981

(22) Filed: Nov. 9, 2006

(65) Prior Publication Data

US 2007/0117819 A1 May 24, 2007

Related U.S. Application Data

(60) Provisional application No. 60/734,763, filed on Nov. 9, 2005.

(51) Int. Cl.
*A61K 31/195* (2006.01)
*A61K 31/19* (2006.01)
*A01N 37/12* (2006.01)
*A01N 37/44* (2006.01)
*A01N 37/10* (2006.01)

(52) U.S. Cl.
USPC ............................. 514/563; 514/571; 514/566

(58) Field of Classification Search
USPC ........................................ 514/563, 566, 571
See application file for complete search history.

(56) References Cited

U.S. PATENT DOCUMENTS

| | | | |
|---|---|---|---|
| 4,921,997 | A | 5/1990 | Lalezari et al. |
| 5,093,367 | A | 3/1992 | Lalezari et al. |
| 5,268,500 | A | 12/1993 | Lalezari et al. |
| 5,272,176 | A | 12/1993 | Ulrich et al. |
| 5,292,935 | A | 3/1994 | Lalezari et al. |
| 5,677,330 | A | 10/1997 | Abraham et al. |
| 5,962,651 | A | 10/1999 | Lalezari et al. |
| 6,337,350 | B1 | 1/2002 | Rahbar et al. |
| 6,589,944 | B1 | 7/2003 | Rahbar |
| 7,320,988 | B2 | 1/2008 | Rahbar et al. |
| 7,652,037 | B2 | 1/2010 | Rahbar et al. |
| 2005/0171150 | A1 * | 8/2005 | Rahbar et al. ................. 514/312 |

OTHER PUBLICATIONS

Figarola et al. (Diaberologia, 2003, 46:1140-52).*
Tanaka et al. (JBC, 275, 33, 25781-790, 2000).*
Schmidt et al. (Atheroscleorsis and Diabetes: The RAGE connection, Current Atherosclerosis Reports, Vascular Biology, p. 430-436, 2,5, Sep. 2000).*
Rahbar, S. et al., "Novel Inhibitors of Advanced Glycation Endproducts," Biochemical and Biophysical Research Communications, 262: 651-656, 1999.
Lalezari, I. et al., "Synthesis and investigation of effects of 2-[4-[[(Arylamino)carbonyl]amino]phenoxy]-2-methylpropionic acids on the affinity of hemoglobin for oxygen: Structure-activity relationships," J. Med. Chem., 32, 2352-2357, 1989.
Al-Abed, Y. et al., "Advanced glycation end products: Detection and reversal," Methods Enzymol., 1999, 309:152-172.
Basta, G. et al., "Advanced glycation end products activate endothelium through signal-transduction receptor RAGE A mechanism for amplification of inflammatory responses," Circulation, 2002, 105:816-822.
Boulanger, E. et al., "AGEs bind to mesothelial cells via RAGE and stimulate VCAM-1 expression," Kidney Int., 2002, 61:148-156.
Brownlee, M., "Biochemistry and molecular cell biology of diabetic complications," Nature, 2001; 414:813-820.
Bucala, R. et al., "Advanced glycosylation: Chemistry, biology and implications for diabetes and aging," Adv. Pharmacol., 1992; 23:1-34.
Bucala, R. et al., "Lipid advanced glycosylation: Pathway for lipid oxidation in vivo," Proc. Natl. Acad. Sci. USA; 1993, 90:6434-6438.
Bucala, R. et al., "Modification of DNA by reducing sugars: a possible mechanism for nucleic acid aging and age-related dysfunction in gene expression," Proc. Natl. Acad. Sci. USA, 1984; 81: 105-109.
Rahbar, S. et al., "Novel inhibitors of advanced glycation endproducts," Arch. Biochem. Biophys., 2003; 419: 63-79.
Rahbar, S. et al., "Inhibitors and breakers of advanced glycation endproducts (AGEs): A review," Curr. Med. Chem. Immunol. Edocr. Metabol. Agents, 2002; 2:135-161.
Vlassara, H. "The AGE-receptor in the pathogenesis of diabetic complications," Diabetes Metab. Res. Rev., 2001, 17:436-443.
Wautier, M.P. et al., "Activation of NADPH oxidase by AGE links oxidant stress to altered gene expression via RAGE," Am. J. Physiol. Endocrinol. Metab., 2001, 280:E685-E694.
Wendt, T.M. et al., "RAGE drives the development of glomerulosclerosis and implicates podocyte activation in the pathogenesis of diabetic nephropathy," Am. J. Pathol., 2003; 162:1123-1137.
Lalezari, I. et al., "LR16, a compound with potent effects on the oxygen affinity of hemoglobin, on blood cholesterol, and on low density lipoprotein," Proc. Natl. Acad. Sci. USA, Aug. 1998; 85:6117-6121.
Rahbar, S. et al., "Novel Inhibitors of Advanced Glycation Endproducts (Part II)," Molecular Cell Biology Research Communications, 2000, vol. 3, pp. 360-366, copyright 2000 by Academic Press.

* cited by examiner

*Primary Examiner* — Sreeni Padmanabhan
*Assistant Examiner* — Uma Ramachandran
(74) *Attorney, Agent, or Firm* — Rothwell, Figg, Ernst & Manbeck P.C.

(57) ABSTRACT

Accelerated formation of advanced glycation/lipoxidation end products (AGEs/ALEs) has been implicated in the pathogenesis of various diabetic complications. Several natural and synthetic compounds have been proposed and tested as inhibitors of AGE/ALE formation. We have previously reported the therapeutic effects of several new AGE/ALE inhibitors on the prevention of nephropathy and dyslipidemia in streptozotocin (STZ)-induced diabetic rats. In this study, we investigated the effects of various concentrations of LR-90 on the progression of renal disease and its effects on AGE and receptor for AGE (RAGE) protein expression on the kidneys of diabetic STZ-rats. In vitro studies were also performed to determine if LR-90 could inhibit the expression of various pro-inflammatory mediators in human monocytic cells.

1 Claim, 10 Drawing Sheets

ND

D + LR-90 (10 mg)

D

D + LR-90 (25 mg)

D + LR-90 (2.5 mg)

D + LR-90 (50 mg)

ND

D + LR-90 (10 mg)

D

D + LR-90 (25 mg)

D + LR-90 (2.5 mg)

D + LR-90 (50 mg)

SEQUENCE LISTING

<160> NUMBER OF SEQ ID NOS: 10

<210> SEQ ID NO 1
<211> LENGTH: 24
<212> TYPE: DNA
<213> ORGANISM: Homo sapiens

<400> SEQUENCE: 1
gccttaagta atgttaattc ttat                                           24

<210> SEQ ID NO 2

-continued

```
<211> LENGTH: 24
<212> TYPE: DNA
<213> ORGANISM: Homo sapiens

<400> SEQUENCE: 2
ggtgtaatag ttacaaaata ttca                                          24

<210> SEQ ID NO 3
<211> LENGTH: 21
<212> TYPE: DNA
<213> ORGANISM: Homo sapiens

<400> SEQUENCE: 3
aagcccctgg tgcctaatga g                                             21

<210> SEQ ID NO 4
<211> LENGTH: 20
<212> TYPE: DNA
<213> ORGANISM: Homo sapiens

<400> SEQUENCE: 4
caccaattgg acctcctcca                                               20

<210> SEQ ID NO 5
<211> LENGTH: 20
<212> TYPE: DNA
<213> ORGANISM: Homo sapiens

<400> SEQUENCE: 5
atctaccctc ctcaagtccc                                               20

<210> SEQ ID NO 6
<211> LENGTH: 21
<212> TYPE: DNA
<213> ORGANISM: Homo sapiens

<400> SEQUENCE: 6
taccagaagg gcaggataca g                                             21

<210> SEQ ID NO 7
<211> LENGTH: 20
<212> TYPE: DNA
<213> ORGANISM: Homo sapiens

<400> SEQUENCE: 7
caacaagagt tcgaagacaa                                               20

<210> SEQ ID NO 8
<211> LENGTH: 20
<212> TYPE: DNA
<213> ORGANISM: Homo sapiens

<400> SEQUENCE: 8
cccctTcttc ttcatctgta                                               20

<210> SEQ ID NO 9
<211> LENGTH: 22
<212> TYPE: DNA
<213> ORGANISM: Homo sapiens

<400> SEQUENCE: 9
tgaaaaagaa gggtgagaag ag                                            22

<210> SEQ ID NO 10
```

```
<211> LENGTH: 20
<212> TYPE: DNA
<213> ORGANISM: Homo sapiens

<400> SEQUENCE: 10
ggaagatggg aaaggtgagg                                           20
```

METHODS OF SUPPRESSION OF RAGE GENE EXPRESSION AND RAGE TRIGGERED INFLAMMATORY GENES BY SELECTED AGE-INHIBITORS

CROSS REFERENCE TO RELATED APPLICATION

This application claims benefit of U.S. Provisional Patent Application No. 60/734,763, filed Nov. 9, 2005, which is hereby incorporated by reference in its entirety into the present application.

BACKGROUND OF THE INVENTION

1. Technical Field

The invention relates to the field of biomedical sciences, and in particular relates to novel advanced glycation end product ("AGE"), inhibitors methods for suppression of expression of a gene encoding the receptor for advanced glycation end products (RAGE), and suppression of pro-inflammatory signals and genes triggered by RAGE including NF-kB, MCP-1, TNF-a, NADPH-oxidase.

2. Description of the Background Art

Advanced glycation end products (AGEs), the products of non-enzymatic glycation and oxidation of proteins and lipids, accumulate in diverse biological settings, such as diabetes, inflammation, renal failure and aging. Ahmed N, *Diabetes Res Clin Pract.* 67:3-21, 2005; Vlassara H, *J Intern Med.* 251:87-101, 2001. AGEs have been proposed to play a crucial role in the pathogenesis of diabetic vascular complications and atherogenesis in non-diabetic subjects. Rojas A, Morales M A., *Life Sci.* 76: 715-730, 2004; Yamagishi S, Imaizumi T, *Curr Pharm Des* 11: 2279-2299, 2005. Patients with diabetes exhibit an increased propensity to develop atheroschlerosis, with its sequelae acute myocardial infarction and stroke. Basta G, Schmidt A M, De Caterina R, *Cardiovasc Res.* 63: 582-592, 2004; Jakus V, Rietbrock N. *Physiol Res.* 53:1131-142, 2004.

Non-enzymatic glycation (also known as the Maillard reaction) is a complex series of reactions between reducing sugars and the amino groups of proteins, lipids, and DNA which leads to browning, fluorescence and cross-linking. Bucala et al., *Proc. Natl. Acad. Sci. USA* 90:6434-6438, 1993; Bucala et al., *Proc. Natl. Acad Sci. USA* 81:105-109, 1984; Singh et al., *Diabetologia* 44:129-146, 2001. This complex cascade of condensations, rearrangements and oxidation produces heterogeneous, irreversible, proteolysis-resistant, antigenic products known as advanced glycation end products. Singh et al., *Diabetologica* 44:129-146, 2001; Ulrich and Cerami, *Rec. Prog. Hormone Res.* 56:1-2, 2001. Examples of these AGEs are $N^\epsilon$-(carboxymethyl) lysine (CML), $N^\epsilon$-(carboxyethyl) lysine (CEL), $N^\epsilon$-(carboxymethyl)cysteine (CMC), arg-pyrimidine, pentosidine and the imidazolium crosslinks methyl-gloxal-lysine dimer (MOLD) and glyoxal-lysine dimer (GOLD). Thorpe and Baynes, *Amino Acids* 25:275-281, 2002; Chellan and Nagaraj, *Arch. Biochem. Biophys.* 368:98-104, 1999. This type of glycation begins with the reversible formation of a Schiff's base, which undergoes a rearrangement to form a stable Amadori product.

Both Schiff's bases and Amadori products further undergo a series of reactions through dicarbonyl intermediates to form AGEs. Lipid peroxidation of polyunsaturated fatty acids (PUFA), such as arachidonic acid and linoleic acid, also yield carbonyl compounds. Some of these compounds are identical to those formed from carbohydrates, such as MG and GO, and others are characteristic of lipid, such as malondialdehyde (MDA), 4-hydroxynonenal (HNE), and 2-hydroxyheptanal (2HH). See Baynes and Thorpe, *Free Rad. Biol. Med.* 28:1708-1716, 2000; Fu et al., *J. Biol. Chem.* 271:9982-9986, 1996; Miyata et al., *FEBS Lett.* 437:24-28, 1998; Miyata et al., *J. Am. Soc. Nephrol.* 11:1744-1752, 2000; Requena et al., *Nephrol. Dial. Transplant.* 11 (supp. 5):48-53, 1996; Esterbauer et al., *Free Radic. Biol. Med.* 11:81-128, 1991; Requena et al., *J. Biol. Chem.* 272:17473-14779, 1997; Slatter et al., *Diabetologia* 43:550-557, 2000. These reactive carbonyl species (RCSs) rapidly react with lysine and arginine residues of proteins, resulting in the formation of advanced lipoxidation end products (ALEs) such as $N^\epsilon$-carboxymethyllysine (CML), $N^\epsilon$-carboxyethyllysine (CEL), GOLD, MOLD, malondialdehyde-lysine (MDA-lysine), 4-hydroxynonenal-lysine (4-HNE-lysine), hexanoyl-lysine (Hex-lysine), and 2-hydroxyheptanoyl-lysine (2HH-lysine). Thorpe and Baynes, *Amino Acids* 25:275-281, 2002; Miyata et al., *FEBS Lett.* 437:24-28, 1998; Miyata et al., *J. Am. Soc. Nephrol.* 11:1744-1752, 2000; Uchida et al., *Arch. Biochem. Biophys.* 346:45-52, 1997; Baynes and Thorpe, *Free Rad. Biol. Med.* 28:1708-1716, 2000. Since CML, CEL, GOLD and MOLD can result from lipid and carbohydrate metabolism, these chemical modifications on tissue proteins can serve as biomarkers of oxidative stress resulting from sugar and lipid oxidation. Fu et al., *J. Biol. Chem.* 271:9982-9986, 1996; Requena et al., *Nephrol. Dial. Transplant.* 11 (supp. 5):48-53, 1996.

In human diabetic patients and in animal models of diabetes, these non-enzymatic reactions are accelerated and cause accumulation of AGEs on long-lived structural proteins such as collagen, fibronectin, tubulin, lens crytallin, myelin, laminin and actin, in addition to hemoglobin, albumin, LDL-associated proteins and apoprotein. The structural and functional integrity of the affected molecules, which often have major roles in cellular functions, are perturbed by such modifications, with severe consequences on organs such as kidney, eye, nerve, and micro-vascular functions, which consequently leads to various diabetic complications such as nephropathy, atherosclerosis, microangiopathy, neuropathy and retinopathy. Boel et al., *J. Diabetes Complications* 9:104-129, 1995; Hendrick et al., *Diabetologia* 43:312-320, 2000; Vlassara and Palace, *J. Intern. Med.* 251:87-101, 2002.

Research results indicate that reactive carbonyl species such as MGO, GO, GLA, dehydroascorbate, 3-deoxyglucosone and malondialdehyde, are potent precursors of AGE/ALE formation and protein crosslinking. Lyons and Jenkins, *Diabetes Rev.* 5:365-391, 1997; Baynes and Thorpe, *Diabetes* 48:1-9, 1999; Miyata et al., *J. Am. Soc. Nephrol.* 11:1744-1752, 2000; Thornalley st al., *Biochem. J.* 344:109-116, 1999. In vitro studies further suggest that these carbonyl originate mainly from ascorbate and polyunsaturated fatty acids and not from glucose per se. Miyata et al., *FEBS Lett.* 437:24-28, 1993.

Direct evidence implicates the contribution of AGEs/ALEs in the progression of diabetic complications in different lesions of the kidneys, the rat lens, and in atherosclerosis. Horie et al., *J. Clin. Invest.* 100:2995-3004, 1997; Matsumoto et al., *Biochem. Biophys. Res. Commun.* 241:352-354, 1997; Bucala and Vlassara, *Exper. Physiol.* 82:327-337, 1997; Bucala and Rahbar, in: *Endocrinology of Cardiovascular Function*. E. R. Levin and J. L. Nadler (eds.), 1998. Kluwer Acad. Publishers, pp. 159-180; Horie et al., *J. Clin. Invest.* 100:2995-3004, 1997; Friedman, *Nephrol. Dial. Transplant.* 14 (supp. 3):1-9, 1999; Kushiro et al., *Nephron* 79:458-468, 1998. Several lines of evidence indicate that hyperglycemia in diabetes causes the increase in reactive carbonyl species (RCS) such as methylglyoxal, glycolaldehyde, glyoxal, 3-deoxyglucosone, malondialdehyde, and hydroxynonenal.

"Carbonyl stress" leads to increased modification of proteins and lipids, through reactive carbonyl intermediates forming adducts with lysine residues of proteins, followed by oxidative stress and tissue damage. Lyons and Jenkins, *Diabetes Rev.* 5:365-391, 1997; Baynes and Thorpe, *Diabetes* 48:1-9, 1999; Miyata et al., *J. Am. Soc. Nephrol.* 11:1744-1752, 2000.

Through generation of reactive oxygen species (ROS), reactive carbonyl species (RCS) and reactive nitrogen species (RNS), AGEs contribute to tissue injury by alteration of extracellular matrix structures through formation of protein crosslinks, and alteration of intracellular short-lived proteins such as metabolic enzymes and mitochondrial protein complexes. DeGroot J. *Curr Opin Pharmacol.* 4: 301-305, 2004; Rosca M G, Mustata T G, Kinter M T, et al., *Am J Physiol Renal Physiol.* 289: F420-F430, 2005. Multiple receptor independent and receptor dependent pathways linking AGEs/ALEs to cellular and tissue dysfunction have been proposed. Schmidt A M, Hori O, Brett J, et al. *Arterioscler Thromb* 14: 1521-1528, 1994; Vlassara H., *Diabetes Metab Res Rev.* 17: 436-443, 2001. Modulation of cellular functions through interactions with specific cell surface receptors, the best characterized of which is the receptor of AGE (RAGE), has been extensively explored. Schmidt A M, Yan S D, Yan S F, Stern D M., *Biochim. Biophys.* 1498:99-111, 2000; Kim W, Hudson B, Moser B, et al., *Ann N Y Acad Sci.* 1043: 553-561, 2005; Bucciarelli L G, Wendt T, Rong L, et al., *Cell Mol Life Sci.* 59: 1117-1128, 2002.

Binding of AGEs to RAGE activates intracellular signaling processes, thus mediating pro-inflammatory AGE effects. Basta G, Lazzerini G, Massaro M, et al., *Circulation* 105: 816-822, 2002; Chavakis T, Bierhaus A, Nawroth P P, *Microbes Infect.* 6: 1219-1225, 2004. Previous work has demonstrated that RAGEs are present at low levels on the surface of vascular cells, smooth muscle cells, fibroblasts, and monocyte/macrophages. Bucciarelli L G, Wendt T, Rong L, et al., *Cell Mol Life Sci.* 59: 1117-1128, 2002.

In endothelial cells, tumor necrosis factor-α (TNF-α) as well as AGEs themselves, upregulate RAGE expression, thus rendering these cells more susceptible to pro-inflammatory AGE effects Basta G, Schmidt A M, De Caterina R., *Cardiovasc Res.* 63: 582-592, 2004. In addition to AGEs, peptides like S100/calgranulins, β-amyloid, and amphoterin have been shown to activate RAGE. Liliensiek B, Weigand M A, Bierhaus A, et al., *J Clin Invest.* 113: 1641-1650, 2004. In endothelial cells, binding of RAGEs to these ligands activates the transcription factor nuclear factor-κb (NF-κb), subsequently leading to increased expression of pro-atherogenic mediators such as monocyte chemoattractant protein-1 (MCP-1) or vascular cell adhesion molecule-1 (VCAM-1) Basta G, Lazzerini G, Massaro M, et al., Circulation 105: 816-822, 2002; Wautier J L, Schmidt A M. 2004. Circ Res. 95:233-238, 2004.

AGE formation has been proposed to be the key step in creating a nidus for the amplification of stress pathways and is hypothesized to be involved in a vicious cycle of AGE→inflammation→ROS→AGE→ more inflammation. Ramasamy R, Vannucci S J, Yan S S, et al., *Glycobiology.* 15:16R-28R, 2005. In vitro experiments as well as animal data suggest that limiting RAGE expression in vascular cells might be an intriguing concept to modulate atherogenesis and inflammatory disorders Hudson B I, Schmidt A M., *Pharm Res.* 21: 1079-1086, 2005. Suppression of enhanced expression of endothelial RAGE has been achieved by using extracellular domain of RAGE (sRAGE) Park L, et al., *Nat. Med.* 4: 1025-1031, 2001; Bucciarelli L G, Wendt T, Qu W, et al., *Circulation* 106: 2827-2835, 2001, anti RAGE IgG antibody (Rong L L, Trojaborg W, Qu W, et al., *FASEB J.* 18:11812-11817, 2004) and by thiazolidinediones like pioglitazone and roziglitazone. Marx N, Walcher D, Ivanova N, et al., *Diabetes* 53: 2662-2668, 2004.

Over the years, several natural and synthetic compounds have been proposed and advanced as potential AGE/ALE inhibitors. These include aminoguanidine, pyridoxamine, OPB-9195, carnosine, metformin, as well as some angiotensin-converting enzyme inhibitors (ACEI) and angiotensin II type 1 receptor blockers (ARB), derivatives of aryl (and heterocyclic) ureido, and aryl (and heterocyclic) carboxamido phenoxyisobutyric acids. Rahbar et al., *Biochem. Biophys. Res. Commun.* 262:651-656, 1999; Rahbar et al., *Mol. Cell. Biol. Res. Commun.* 3:360-366, 2000; Rahbar and Figarola, *Curr. Med. Chem.* (Immunol. Endocr. Metabol. Agents) 2:135-161, 2002; Rahbar and Figarola, *Curr. Med. Chem.* (Immunol. Endocrin. Metabol.) 2:174-186, 2002; Forbes et al., *Diabetes* 51:3274-3282, 2002; Metz et al., *Arch. Biochem. Biophys.* 419:41-49; Nangaku et al., *J. Am. Soc. Nephrol.* 14:1212-1222, 2003; Rahbar and Figarola, *Arch. Biochem. Biophys.* 419:63-79, 2003. Recently, some of these compounds were found to be effective AGE inhibitors in vivo and to prevent the development of diabetic nephropathy in a streptozotocin-induced diabetes.

Over the last decade, evidence has accumulated implicating AGEs/ALEs as major factors in the pathogenesis of diabetic nephropathy and other complications of diabetes. Administration of AGEs to non-diabetic rats leads to glomerulosclerosis and albuminuria, indicating that AGEs alone may be sufficient to cause renal injury in diabetes. Vlassara et al., *Proc. Natl. Acad. Sci. USA* 91:11704-11708, 1994. Diabetic animals fed with a diet low in glycoxidation products developed minimal symptoms of diabetic nephropathy compared with animals fed with diet high in glycoxidation products. Zheng et al., *Diabetes Metab. Res. Rev.* 18:224-237, 2002. It is widely accepted that AGEs/ALEs contribute to diabetic tissue injury by at least two major mechanisms. Browlee, *Nature* 414:813-820, 2001; Stith et al., Expert Opin. Invest. Drugs 11:1205-1223, 2002; Vlassara and Palace, *J. Intern. Med.* 251:87-101, 2002. The first is receptor-independent alterations of the extracellular matrix architecture and function of intracellular proteins by AGE/ALE formation and AGE/ALE-protein crosslinking. The other is receptor-dependent modulation of cellular functions through interaction of AGE with various cell surface receptors, especially RAGE. Wendt et al., *Am. J. Pathol.* 162:1123-1137, 2003; Vlassara, *Diabetes Metab. Res. Rev.* 17:436-443, 2001; Kislinger et al., *J. Biol. Chem.* 274:31740-3174, 1999.

Advanced glycation/lipoxidation end products (AGEs/ALEs) also have been implicated in the pathogenesis of a variety of debilitating diseases such as atherosclerosis, Alzheimer's and rheumatoid arthritis, as well as the normal aging process. The pathogenic process is accelerated when elevated concentrations of reducing sugars or lipid peroxidation products are present in the blood and in the intracellular environment such as occurs with diabetes. Both the structural and functional integrity of the affected molecules become perturbed by these modifications and can result in severe consequences in the short and long term. Because hyperlipidemia, hyperglycemia, diabetes and syndromes such as "metabolic syndrome" are common and are a common cause of morbidity and mortality, methods to counteract the symptoms and consequences of these metabolic states are needed in the art.

New classes of compounds as inhibitors of AGE formation and protein crosslinking have been reported previously. Rahbar S, Figarola J L., *Arch Biochem Biophys.* 419: 63-79, 2003.

More recently, several of these LR compounds were found effective in preventing the development of diabetic nephropathy in STZ-induced diabetic animals Figarola J L, Scott S, Loera S, et al., *Diabetologia* 46: 1140-1152m 2005; Figarola J L, Scott S, Loera S, et al., *Diabetes Metab Res Rev.* 21: 533-544, 2005. To date, methylene bis (4,4'-(2-chlorophenylureidophenoxy-isobutyric acid) (referred to herein as "LR-90") has been found to be the most powerful among all other compounds in the LR-series.

SUMMARY OF THE INVENTION

LR-90 has now been investigated in vivo using a concentration-dependent response of the drug in STZ-induced diabetic rats and examined its efficacy in protecting against kidney pathology and its effect on lipid concentrations on these diabetic animals (FIG. 1). The ability of the compound to inhibit tissue AGE accumulation and to suppress the expression of RAGE in the kidneys of diabetic rats through immunohistochemical methods also has been examined. In addition, the ability of LR-90 to inhibit RAGE, NADPH oxidase, COX-2 and MCP-1 expressions in S100b-induced THP-1 human monocytic cells has been investigated.

Accordingly, in one embodiment, the invention provides a method of suppressing gene expression of RAGE in a mammal comprising administering to the mammal an effective amount of LR-90.

In another embodiment, the invention provides a method of treating complications resulting from diabetes which result from RAGE protein expression, the method comprising administering an effective amount of LR-90.

In yet another embodiment, the invention provides a method of treating a patient with Alzheimer's Disease, athereroschlerosis or diseases associated with chronic inflammatory disorders, which comprises administering an effective amount of LR-90 [methylene bis (4,4'-(2-chlorophenylureidophenoxyisobutyric acid)].

In yet another embodiment, the invention provides a method of suppressing pro-inflammatory signals and genes triggered by RAGE including NADPH oxidase, COX-2, and MCP-1 which comprises administering an effective amount of LR-90.

In in vivo studies investigating the effects of LR-90 in streptozotocin-induced diabetic rats, the compound not only was able to inhibit tissue AGE accumulation and to suppress the expression of RAGE, but also inhibited early renal disease and efficiently reduced the increased concentrations of triglycerides and cholesterol in diabetic animals by more than 50%, preventing the complications normally seen in diabetes and in aging.

BRIEF DESCRIPTION OF THE DRAWINGS

FIG. 1 is a diagram showing a randomized study which the diabetic rats under treatment in 5 groups of ten each: one diabetic control group (0 mg/L), one group receiving 2.5 mg/L, one group receiving 10 mg/L, a third group receiving 20 mg/L and a fourth group receiving 50 mg/L of LR-90 in drinking water.

FIG. 2 shows kidneys of diabetic animals exhibiting severe mesangial expansion and glomerulosclerosis as evidenced by increased accumulation of PAS-positive materials in the mesangial area of the glomeruli (data not shown) and increased collagen deposition and tubular degeneration in the glomeruli as revealed by Trichrome staining.

FIG. 3 shows the effect of various concentrations of LR-90 on plasma lipids. With the exception of 10 mg/L treatment, all concentrations tested nearly normalized the cholesterol concentration to that of non-diabetic animals.

FIG. 4 shows immunohistochemical staining for AGEs in rat kidney demonstrated that there was widespread staining for these markers in the kidney glomeruli and cortical tubules in diabetic rats compared with the non-diabetic control rats.

FIG. 5 shows RAGE protein expression in the glomeruli visibly higher in diabetic rats compared with non-diabetic animals.

FIG. 6 shows the effects of LR-90 on S100b-induced RAGE mRNA expression on THP-1 monocytes. Representative RT-PCT (upper panel); average densitometer readings of three separate experiments (lower panel). * $P<0.01$ vs. Ctrl;  $P<0.05$ vs. S100b; * $P<0.01$ vs. S100b.

FIG. 7 shows the effects of LR-90 on S100b-induced MCP-1 mRNA expression on THP-1 monocytes. Representative RT-PCR (upper panel); Average densitometer readings of three separate experiments (middle panel); Secreted MCP-1 protein detected using specific ELISA (lower panel). * $P<0.01$ vs. Ctrl;  $P<0.05$ vs. S100b; * $P<0.01$ vs. S100b.

FIG. 8 shows the effects of LR-90 on S100b-induced NADPH oxidase mRNA expression on THP-1 monocytes. Representative RT-PCR (upper panel); Average densitometer readings of two separate experiments (lower panel). * $P<0.01$ vs. Ctrl; ** $P<0.05$ vs. S100b.

FIG. 9 shows the effects of LR-90 on S100b-induced COX-2 mRNA expression on THP-1 monocytes. Representative RT-PCR (upper panel); Average densitometer readings of two separate experiments (lower panel). * $P<0.01$ vs. Ctrl; ** $P<0.05$ vs. S100b.

FIG. 10 shows the effects of LR-90 on THP-1 monocytes. Cells treated with various concentrations of LR-90 were counted after 24 hours (upper panel) and the number of viable cells were determined by hemocytometer counts of Trypan Blue-impermeable cells (lower panel). Average counts of two separate experiments.

DETAILED DESCRIPTION OF THE PREFERRED EMBODIMENTS

Figure 1:
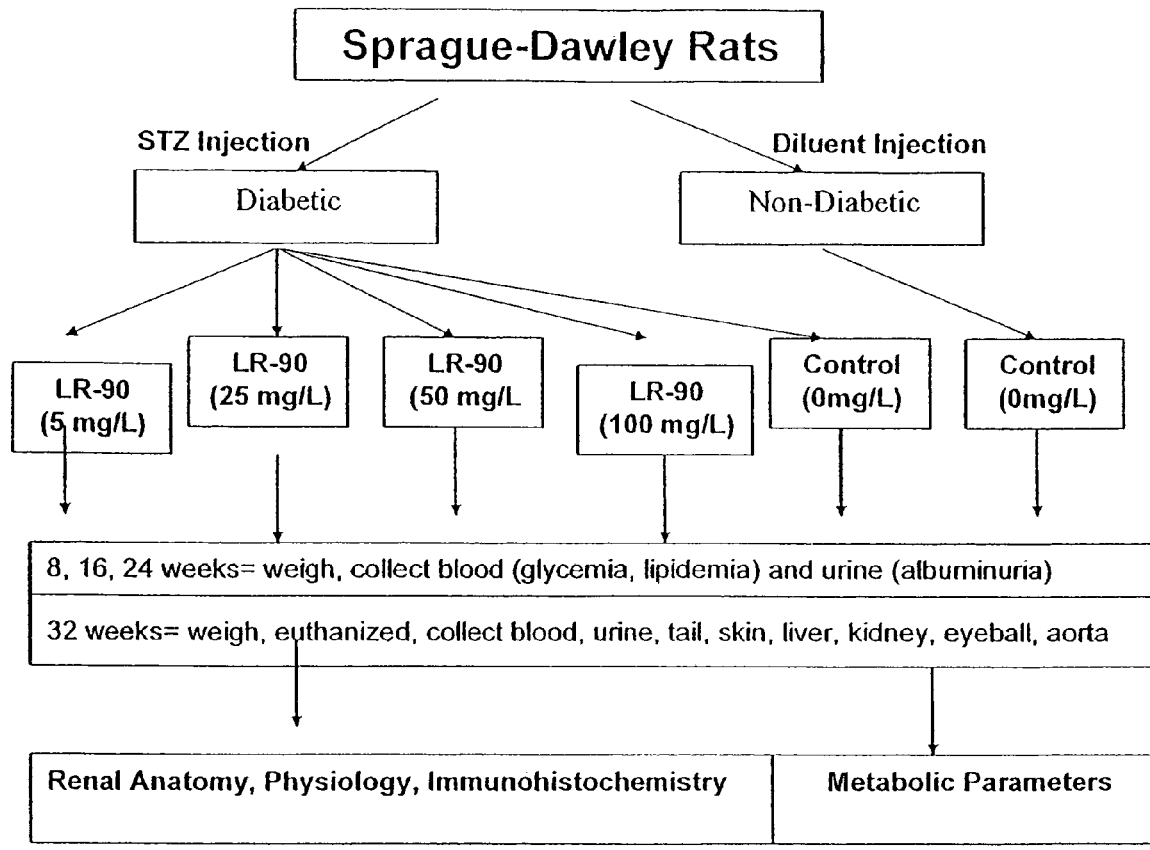
FIG. 1: Experimental Design.

LR-90 belongs to a group of novel aromatic compounds derived from "LR-16" or N-4-(nitrophthalimido)phenoxy-isobutyric acid. LR-16 acts as an allosteric effector, synergistic with 2,3-bisphosphoglycerate in increasing the oxygen affinity of hemoglobin molecules, and which has been shown to lower serum cholesterol and low-density lipoproteins (LDL) in rats which were fed a diet rich in cholesterol.

Lalezari et al., *Proc. Natl. Acad. Sci. USA* 85:6117-6121, 1988.

Diabetic rats treated with LR-90 exhibited statistically significant improvement in renal function in terms of inhibition of an increase in urinary albumin-to-creatine ratio. In addition, histochemical observations show that treatment with LR-90 minimized kidney structural damage as indicated by a reduction in the incidence of glomerulosclerosis, cortical tubule degeneration and collagen deposition in the kidney compared to untreated diabetic rats. Additionally, LR-90 prevented mesangial expansion and basement membrane thickening of the kidneys of diabetic rats. These compounds effectively inhibited the in situ accumulation of immunoreactive AGEs in collagen tissues and kidneys of diabetic rats without any effect on hyperglycemia. LR-90 lowered cholesterol and triglyceride concentrations found in the hyperlipidemia of diabetic rats but did not significantly change in the lipid levels of control non-diabetic rats.

While the present invention is not limited to any particular theory, it has been proposed that two mechanisms for the beneficial effects of LR compounds in preventing diabetic nephropathy are their lipid-lowering activities per se and their AGE inhibitor and antioxidative properties. The AGE/ALE inhibitor pyridoxamine have been also shown to correct hyperlipidemia and nephropathy in both diabetic rats and non-diabetic rats obese rats, probably by interfering with various reactive carbonyl intermediates of AGE/ALE formation from lipid oxidation. Degenhardt et al., *Kidney Int.* 61:939-950, 2002; Alderson et al., *Kidney Int.* 63:2123-2133, 2003.

Thus, in addition to its protective effects on kidneys in diabetic rats, these novel compounds, specifically LR-90 can be used in the treatment of atherosclerosis and other vascular complications of diabetes.

Known AGE inhibitors with renoprotective effects such aminoguanidine, pyridoxamine, and OPB-9195 are thought to prevent AGE/ALE accumulation by interacting with highly reactive RCS and acting as carbonyl traps, preventing AGE/ALE formation. However, the metal chelation properties of these AGE inhibitors may contribute to their effectiveness in preventing AGE formation in vivo. The mechanism of action of these LR compounds, including LR-90 is still unclear, but the LR compounds are potent chelators of $Cu^{2+}$ (more potent than AG and PM), and are effective inhibitors of oxidation of ascorbic acid. Moreover, these compounds strongly inhibit hydroxyl radical formation, and LR-90 also may prevent superoxide production. The various pathways involved in the production and generation of protein carbonyls and Amadori products important in the formation of some AGEs and ALEs may require free radicals, transition metals, or both. Miyata et al., *J. Am. So. Nephrol.* 13:2478-2487, 2002; Voziyan et al., *J. Biol. Chem.* (2003 Sep. 15). However, unlike aminoguanidine and pyridoxamine, which act primarily by trapping RCS, these novel LR compounds also reduce the production of RCS by interfering with oxidative metabolism, for example by lowering formation of hydroxyl radicals and interacting with metal ions that can further promote sugar/lipid oxidation reactions.

The effective dosages and modes of administration are in accordance with accepted medical practices taking into account the clinical condition of the individual subject (e.g. severity and course of the disease), the site and method of administration, scheduling of administration, patient age, sex, body weight and other factors known to medical practitioners. Accordingly, the dosages of the compositions of the invention for treatment of a subject are to be titrated to the individual subject. For example, the interrelationship of dosages for animals of various sizes and species and humans based on $mg/m^2$ of surface area is described by Freireich et al., *Cancer Chemother. Rep.* 50 (4):219-244 (1966). The "effective dose" can be determined by procedures known in the art, and are such as to achieve a discernible change in the disease state.

In addition to their effects on AGE formation and lipid metabolism, LR treatment, specifically LR-90 also may influence some steps in the inflammation pathways leading to tissue injury. LR-90 also prevented cell infiltration in the renal interstitium of diabetic rats. Previous results indicate that S100b treatment upregulated the expression of several groups of genes, including adhesion molecules, chemokines and their receptors and other signaling molecules and enzymes. LR-90 has been shown to suppress or downregulate the expression of genes encoding several of these pro-inflammatory mediators that have been known to be involved in diabetic atherosclerosis and oxidative stress.

Figure 6:
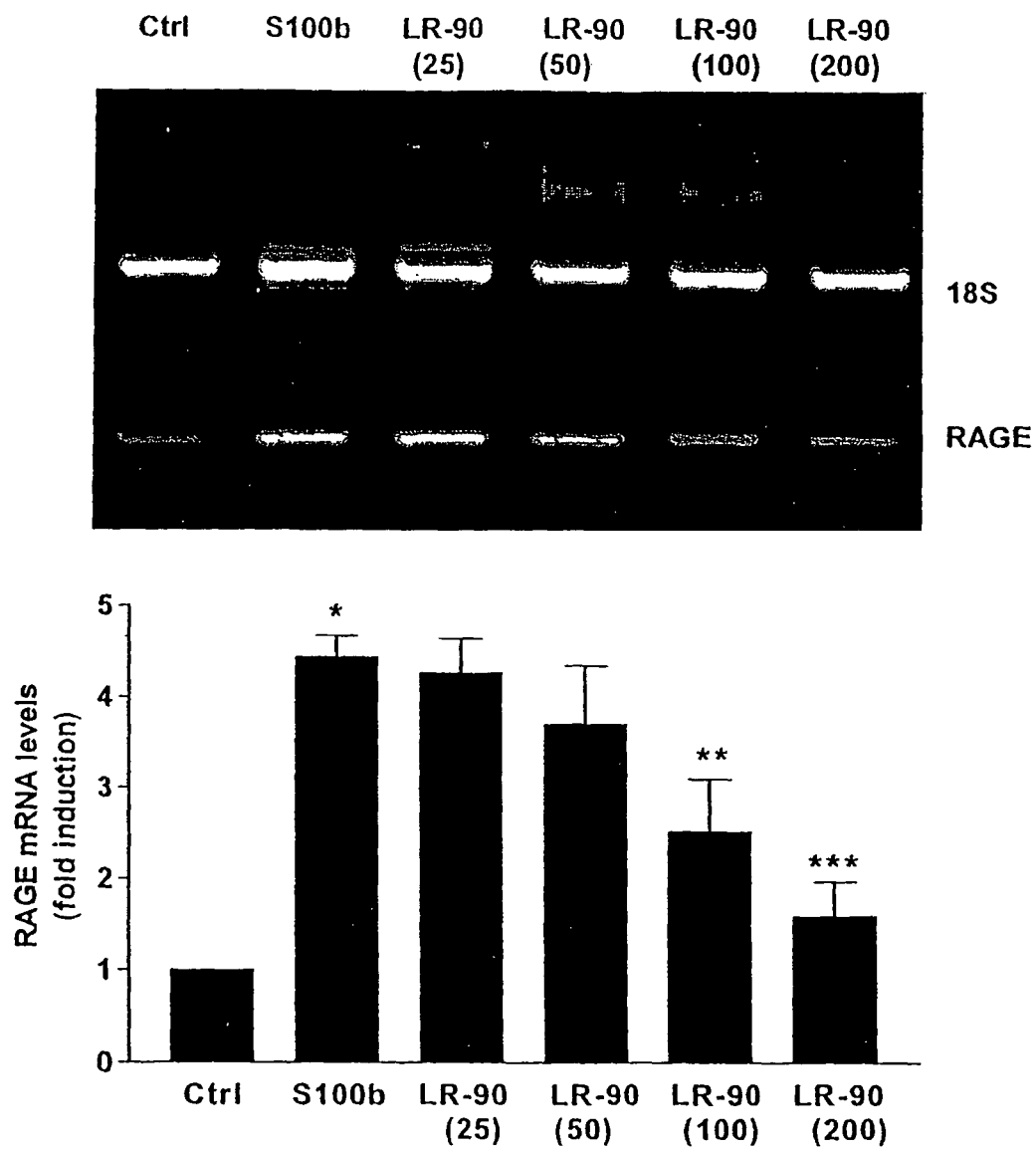
FIG. 6: Effects of LR-90 on S100b-induced RAGE mRNA expression on THP-1 monocytes.
Figure 7:
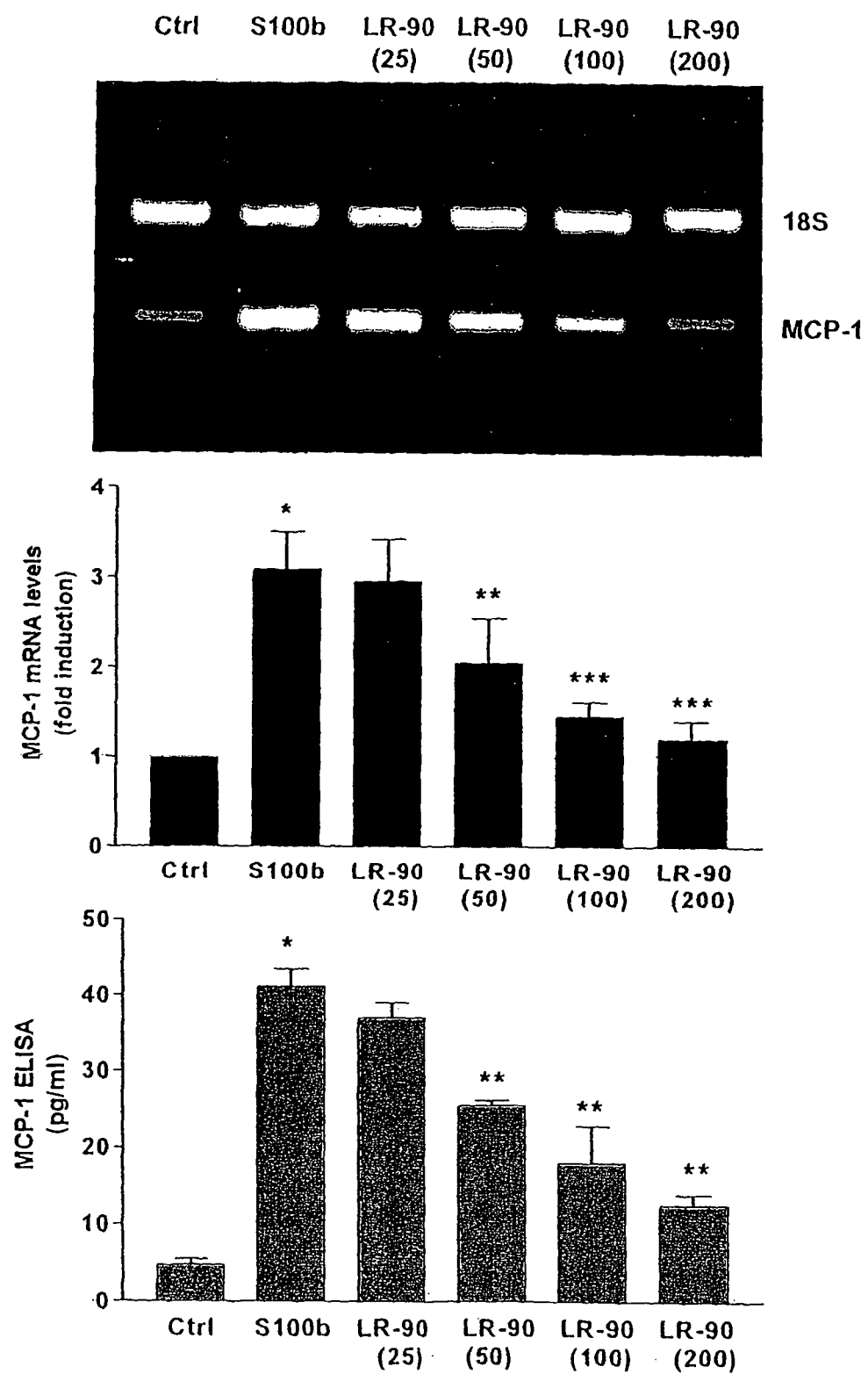
FIG. 7: Effects of LR-90 on S100b-induced MCP-1 mRNA expression on THP-1 monocytes.
Figure 8:
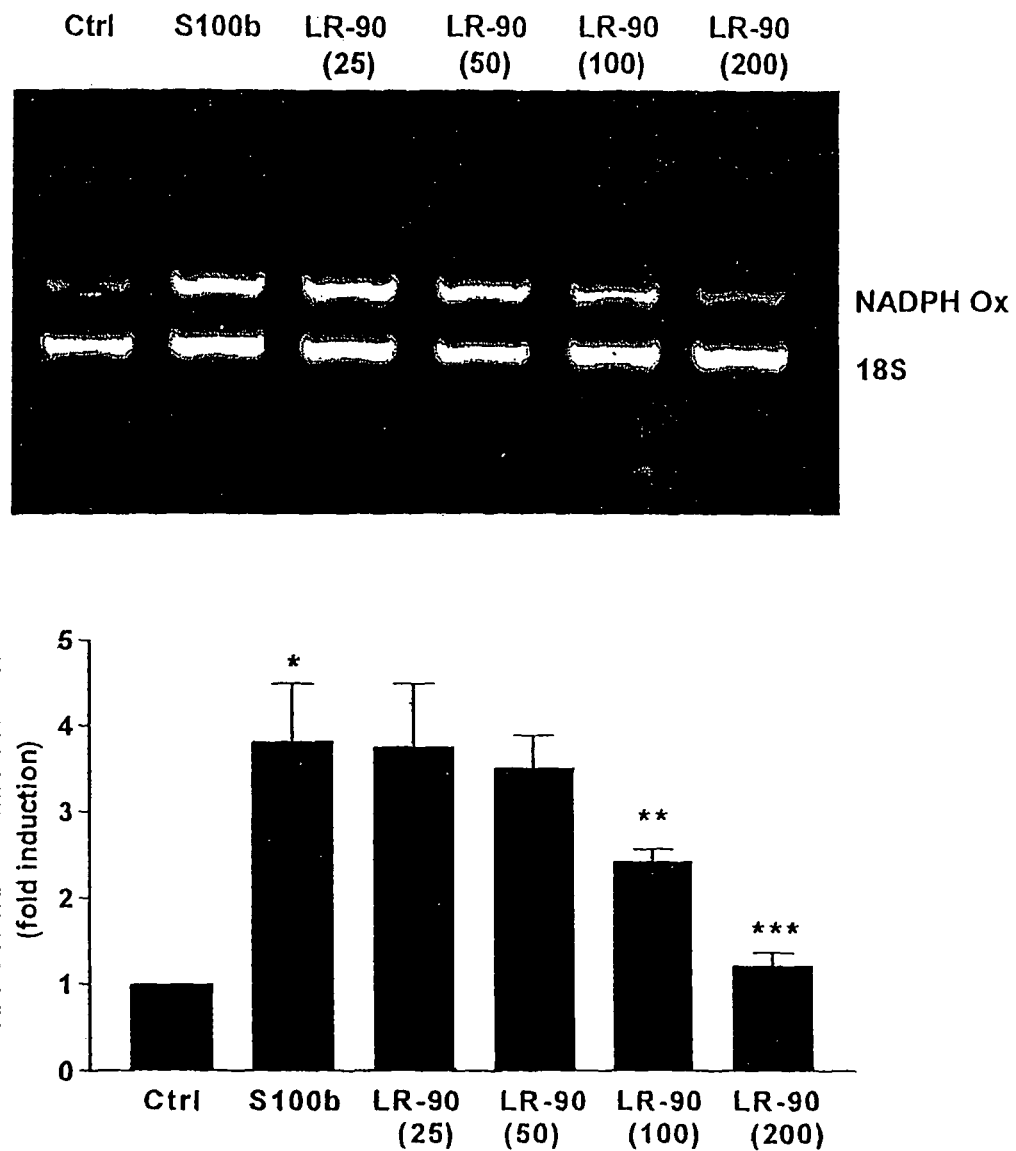
FIG. 8: Effects of LR-90 on S100b-induced NADPH pxidase mRNA expression on THP-1 monocytes.
Figure 9:
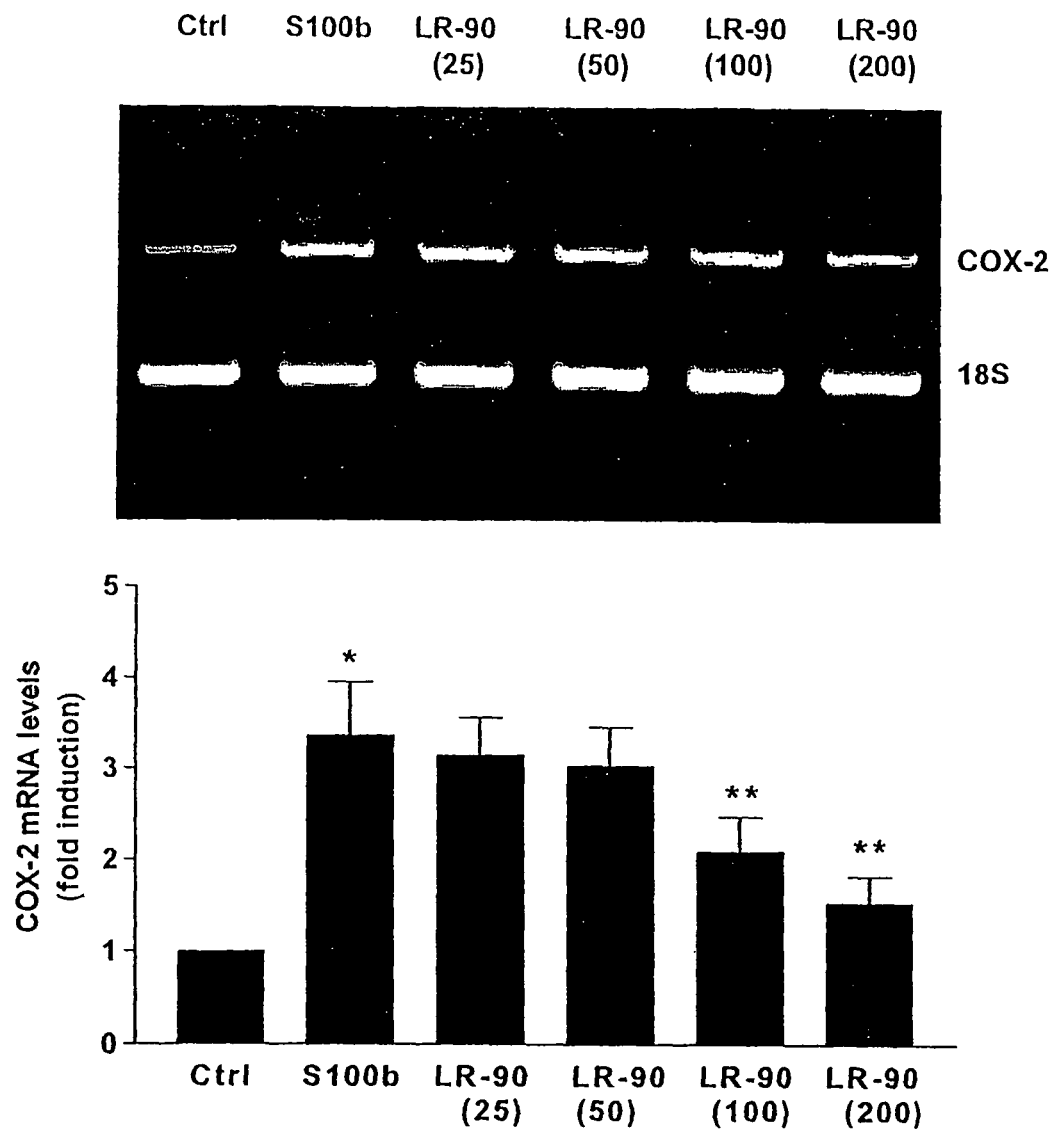
FIG. 9: Effects of LR-90 on S100b-induced COX-2 mRNA expression on THP-1 monocytes.

THP-1 cells incubated with S100b for 4 hours showed increased mRNA expression of RAGE, a known S100b ligand (FIG. 6). Similarly, marked upregulation of the chemokine MCP-1 (FIG. 7), as well as the inflammatory COX-2 enzyme (FIG. 8) and the redox-sensitive NADPH oxidase enzyme (FIG. 9). On the other hand, THP-1 monocytes pre-treated with LR-90 1 hr before S100b incubation profoundly suppressed the expression of all these genes in a concentration-dependent manner, with the highest concentrations tested (100 and 200 ug/ml) exhibiting statistically significant reduction in mRNA expression of the genes analyzed. Interestingly, LR-90 treatment also inhibited MCP-1 protein expression in a concentration-dependent manner (FIG. 7, lower panel).

Figure 10:
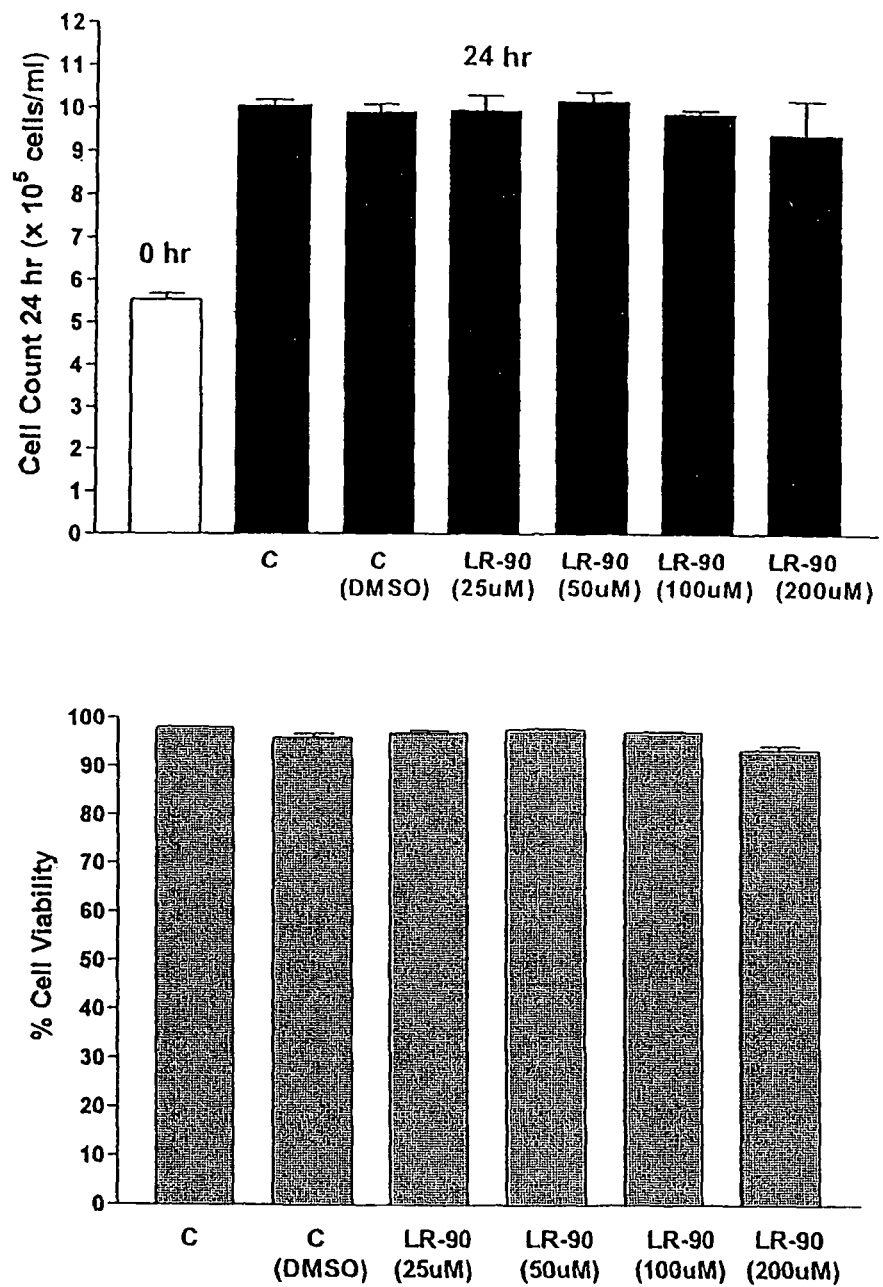
FIG. 10: Effects of LR-90 on THP-1 monocytes.

To confirm that LR-90 indeed suppressed mRNA production of these inflammatory genes by blocking key signaling and/or activation pathways and not by apoptosis or cell toxicity, THP-1 cells were exposed to the same concentrations of LR-90 used in the S100b experiments and incubated the cells for 24 hr. Cell counts after incubation were normal and statistically similar to the untreated cells (FIG. 10, upper panel). Furthermore, Trypan blue staining indicates the LR-90 treated cells were viable (FIG. 10, lower panel).

Oxygen, redox active transition metals and ROS are catalysts of AGE and ALE formation. The various pathways involved in the production and generation of RCS and Amadori products, important in the formation of some AGEs and ALEs, thus may require free radicals, transition metals, or both. However, unlike AG and PM, which act primarily by trapping RCS, the LR compounds, specifically LR-90 also may reduce the product of RCS by interfering with oxidative metabolism. Without being bound by a particular theory, it probably does so by inhibiting formation of free radicals and interacting with metal ions that can further promote sugar/lipid oxidation reactions. The LR compounds have reduced the levels of AGEs/ALEs such as CML and CEL, inhibited the chemical modifications of collagens, and decreased the overall oxidative stress in plasma and kidneys of diabetic animals. All of these effects can influence the thickening and loss of elasticity of the vascular wall, membrane permeability, and inflammatory process (via RAGE interaction), which can lead to the prevention of dyslipidaemia.

Regardless of how the LR compounds, specifically LR-90, lower plasma lipids reactions in vivo, such effects further broaden the possible therapeutic applications of these compounds. Decomposition of lipid peroxides initiates a chain of reactions that produce various RCS that can generate AGEs and ALEs and various lipid adducts which can lead to the accumulation of lipids and lipoproteins in cells in vascular wall. LDL has been identified as the major carrier of lipid hydroperoxides in the plasma and oxidative modification of LDL has been suggested as a causal step in the development of atherosclerosis.

In summary, LR compounds, specifically LR-90, can inhibit AGE accumulation and RAGE protein expression in vivo and also can delay or inhibit the progression of early renal dysfunction in diabetic animals. These compounds also prevent hyperlipidemia and inhibit the overall oxidative stress in these animals. LR-90 can be an effective treatment modality for early renal disease and other diabetic complications where accumulation of AGEs/ALEs, intermediate compounds, and RAGE protein expression are primary contributors. Aside from its AGE-inhibitory properties, LR-90 possesses lipid-lowering characteristics that can influence both the development of diabetic renal disease and atherosclerosis.

REFERENCES

1. Abrass, Cellular lipid metabolism and the role of lipids in progressive renal disease. *Am. J. Nephrol.* 24:46-53, 2004.
2. Ahmed N. 2005. Advanced glycation end products—role in pathology of diabetic complications. Diabetes Res Clin Pract. 67: 3-21.
3. Al-Abed et al., Advanced glycation end products: detection and reversal. *Methods Enzymol.* 309:152-172, 1999.
4. Altomare et al., Increased lipid peroxidation in type 2 poorly controlled diabetic patients. *Diabetes Metab.* 18:264-271, 1992.
5. Anderson et al., The myeloperoxidase system of human phagocytes generates N-epsilon(carboxymethyl)lysine on proteins: a mechanism for producing advanced glycation end products at sites of inflammation. *J. Clin. Invest.* 104: 103-113, 1999.
6. Basta et al., Advanced glycation end products activate endothelium through signal-transduction receptor RAGE: a mechanism for amplification of inflammatory responses. *Circulation* 105:816-822, 2002.
7. Basta G, Schmidt A M, De Caterina R. 2004. Advanced glycation end products and vascular inflammation: implications for accelerated atherosclerosis in diabetes. Cardiovasc Res. 63: 582-592.
8. Baynes and Thorpe, Perspective in diabetes: role of oxidative stress in diabetes complications. A new perspective on an old paradigm. *Diabetes* 48:1-9, 1999.
9. Baynes and Thorpe, Glycoxidation and lipoxidation in atherogenesis. *Free Rad. Biol. Med.* 28:1708-1716, 2000.
10. Boel et al., Diabetic late complications: will aldose reductase inhibitors or inhibitors of advanced glycosylation end product formation hold promise? *J. Diabetes Complications* 9:104-129, 1995.
11. Boulanger et al., AGEs bind to mesothelial cells via RAGE and stimulate VCAM-1 expression. *Kidney Int.* 61:148-156, 2002.
12. Browlee, Biochemistry and molecular cell biology of diabetic complications. *Nature* 414:813-820, 2001.
13. Bucala et al., Modification of DNA by reducing sugars: a possible mechanism for nucleic acid aging and age-related dysfunction in gene expression. *Proc. Natl. Acad Sci. USA* 81: 105-109, 1984.
14. Bucala et al., Lipid advanced glycation pathway for lipid oxidation. *Proc. Natl. Acad. Sci. USA* 90:6434-6438, 1993.
15. Bucala and Vlassara, Lipid and lipoprotein modification by advanced glycation end-products: Role in atherosclerosis. *Exper. Physiol.* 82:327-337, 1997.
16. Bucala and Rahbar, Protein glycation and vascular disease. In: *Endocrinology of cardiovascular function*. E. R. Levin and J. L. Nadler (eds.). (1998) Kluwer Acad. Publishers, pp. 159-180.
17. Bucciarelli L G, Wendt T, Rong L, et al. 2002. RAGE is a multiligand receptor of the immunoglobulin superfamily: implications for homeostasis and chronic disease. Cell Mol Life Sci. 59: 1117-1128.
18. Bucciarelli L G, Wendt T, Qu W, et al. 2001. RAGE blockade stabilizes established atherosclerosis in diabetic apolipoprotein E-null mice. Circulation 106: 2827-2835.
19. Carew et al., Antiatherogenic effect of probucol unrelated to its hypocholesterolemic effect: evidence that antioxidants in vivo can selectively inhibit low density lipoprotein degradation in macrophage-rich fatty streaks and slow the progression of atherosclerosis in the Watanabe heritable hyperlipidemic rabbit. *Proc. Natl. Acad. Sci. USA* 84:7725-7729, 1987.
20. Carpenter et al., Oral alpha-tocopherol supplementation inhibits lipid oxidation in established human atherosclerotic lesions. *Free Radic. Res.* 37:1235-1244, 2003.
21. Chaturvedi et al., Microalbuminuria in type 1 diabetes: rates, risk factors and glycemic threshold. *Kidney Int.* 60:219-227, 2001.
22. Chavakis T, Bierhaus A, Nawroth P P. 2004. RAGE (receptor for advanced glycation end products): a central player in the inflammatory response. Microbes Infect. 6: 1219-1225.
23. Chellan and Nagaraj, Protein crosslinking by the Maillard reaction: dicarbonyl-derived imidazolium crosslinks in aging and diabetes. *Arch. Biochem. Biophys.* 368:98-104, 1999.
24. Chung et al., Single vertical spin density gradient ultracentrifugation. *Methods Enzymol.* 128:181-209, 1978.
25. Creemers et al., Microassay for the assessment of low levels of hydroxyproline. *Biotechniques* 22:656-658, 1997.
26. DeGroot J. 2004. The AGE of the matrix: chemistry, consequence and cure. Curr Opin Pharmacol. 4: 301-305.
27. Dillon et al., Antioxidant properties of aged garlic extract: an in vitro study incorporating human low density lipoprotein. *Life Sci.* 72:1583-1594, 2003.
28. Duffy et al., Iron chelation improves endothelial function in patients with coronary artery disease. *Circulation* 103: 2799-2804, 2001.
29. Esterbauer et al., Chemistry and biochemistry of 4-hydroxynonenal, malonaldehyde and related aldehydes. *Free Radic. Biol. Med.* 11:81-128, 1991.
30. Feng L, Matsumoto C, Schwartz, et al. 2005. Chronic vascular inflammation in patients with type 2 diabetes: endothelial biopsy and RT-PCR analysis. Diabetes Care 28: 379-384.
31. Figarola et al., LR-90, a new advanced glycation end product inhibitor prevents progression of diabetic nephropathy in STZ-diabetic rats. *Diabetologia* 46:1140-1152, 2003.
32. Figarola J L, Scott S, Loera S, et al. 2005. Prevention of early renal disease, dyslipidaemia and lipid peroxidation in STZ-diabetic rats by LR-9 and LR-74, novel AGE inhibitors. Diabetes Metab Res Rev. 21: 533-544.
33. Friedman, Advanced glycation end-products in diabetic nephropathy. *Nephrol. Dial. Transplant.* 14 (Suppl 3):1-9, 1999.
34. Fu et al., The advanced glycation end product, $N^\epsilon$-(carboxymethyl) lysine, is a product of both lipid peroxidation and glycoxidation reactions. *J. Biol. Chem.* 271:9982-9986, 1996.

35. Giardino et al., Aminoguanidine inhibits reactive oxygen species formation, lipid peroxidation, and oxidant-induced apoptosis. *Diabetes* 47:1114-1120, 1998.

36. Gogasyavuz et al., Effects of aminoguanidine on lipid and protein oxidation in diabeic rat kidneys. *Int. J. Exp. Diabetes Res.* 3:145-151, 2002.

37. Heinecke, Oxidants and antioxidants in the pathogenesis of atherosclerosis: implications for the oxidized low density lipoprotein hypothesis. *Atherosclerosis* 141:1-15, 1998.

38. Hendrick et al., Glycation impairs high-density lipoprotein function. *Diabetologia* 43:312-320, 2000.

39. Hicks et al., Catalysis of lipid peroxidation by glucose and glycosylated collagen. *Biochem. Biophys. Res. Commun.* 151:649-655, 1988.

40. Horie et al., Immunohistochemical colocalization of glyoxidation products and lipid peroxidation products in diabetic renal glomerular lesions. *J. Clin. Invest.* 100:2995-3004, 1997.

41. Inouye et al., Glycated hemoglobin and lipid peroxidation in erythrocytes of diabetic patients. *Metabolism* 48:205-209, 1999.

42. Jain et al., Erythrocyte membrane lipid peroxidation and glycosylated hemoglobin in diabetes. *Diabetes* 38:1539-1543, 1989.

43. Jakus V, Rietbrock N. 2004. Advanced glycation end-products and the progress of diabetic vascular complications. Physiol Res. 53:1131-142.

44. Joles et al., Early mechanisms of renal injury in hypercholesterolemic or hypertriglyceridemic rat. *J. Am. Soc. Nephrol.* 11:669-683, 2000.

45. Kawamura et al., Pathophysiological concentrations of glucose promotes oxidative modification of low density lipoprotein by a superoxide-dependent pathway. *J. Clin. Invest.* 942:771-778, 1994.

46. Kennedy and Lyons, Glycation, oxidation, and lipoxidation in the development of diabetic complications. *Metabolism* 46:14-21, 1997.

47. Kim W, Hudson B, Moser B, et al. 2005. Receptor for advanced glycation end products and its ligands: a journey from the complications of diabetes to its pathogenesis. Ann N Y Acad Sci. 1043: 553-561.

48. Kislinger et al., N(epsilon)-(carboxymethyl)lysine adducts of proteins are ligands for receptor for advanced glycation end products that activate cell signaling pathways and modulate gene expression. *J. Biol. Chem.* 274: 31740-3174, 1999.

49. Knott et al., Glycation and glycoxidation of low-density lipoproteins by glucose and low-molecular mass aldehydes. Formation of modified and oxidized particles. *Eur. J. Biochem.* 270:3572-3582, 2003.

50. Kochakian et al., Chronic dosing with aminoguanidine and novel advanced glycosylation end product-formation inhibitors ameliorates cross-linking of tail tendon collagen in STZ-induced diabetic rats. *Diabetes* 45:1694-1700, 1996.

51. Kushiro et al., Accumulation of N sigma-(carboxy-methyl)lysine and changes in glomerular extracellular matrix components in Otsuka Long-Evans Tokushima fatty rat: a model of spontaneous NIDDM. *Nephron* 79:458-468, 1998.

52. Hudson B I, Schmidt A M. 2005. RAGE: a novel target for drug intervention in diabetic vascular disease. Pharm Res. 21: 1079-1086.

53. Lalezari et al., LR16, a compound with potent effects on the oxygen affinity of hemoglobin, on blood cholesterol, and on low density lipoprotein. *Proc. Natl. Acad. Sci. USA* 85:6117-6121, 1988.

54. Lam et al., Cholesterol-lowering therapy may retard the progression of diabetic nephropathy. *Diabetologia* 38:604-609, 1995.

55. Lamb et al., Transistion metal ions within human atherosclerotic lesions can catalyse the oxidation of low-density lipoprotein by macrophages. *FEBS Lett.* 374:12-16, 1995.

56. Liliensiek B, Weigand M A, Bierhaus A, et al. 2004. Receptor for advanced glycation end products (RAGE) regulates sepsis but not the adaptive immune response. J Clin Invest. 113: 1641-1650.

57. Lo et al., The reaction of methylglyoxal with aminoguanidine under physiological conditions and prevention of methylglyoxal binding to plasma proteins. *Biochem. Pharmacol.* 48:1865-1870, 1994.

58. Lopes-Virella et al., Modification of lipoprotein in diabetes. *Diabetes Metab. Rev.* 12:69-90, 1996.

59. Lyons et al., Glycation, oxidation and lipoxidation in the development of the complications of diabetes mellitus: a 'carbonyl stress' hypothesis. *Diabetes Rev.* 5:365-391, 1997.

60. Matsumoto et al., Immunohistochemical evidence for increased formation of advanced glycation end products and inhibition by aminoguanidine in diabetic rat lines. Biochem. *Biophys. Res. Commun.* 241:352-354, 1997.

61. Marx N, Walcher D, Ivanova N, et al. 2004. Thiazolidinediones reduce endothelial expression of receptors for advanced glycation end products. *Diabetes* 53: 2662-2668.

62. Miyata et al., Generation of protein carbonyls by glycoxidation and lipoxidation reactions with autoxidation products of ascorbic acid and polyunsaturated fatty acids. *FEBS Lett.* 437:24-28, 1993.

63. Miyata et al., Advanced glycation and lipoxidation end products: role of reactive carbonyl compounds generated during carbohydrate and lipid metabolism. *J. Am. Soc. Nephrol.* 11:1744-1752, 2000.

64. Miyata et al., Angiotensin II receptor antagonists and angiotensin-converting enzyme inhibitors lower in vitro the formation of advanced glycation end products: biochemical mechanisms. *J. Am. So. Nephrol.* 13:2478-2487, 2002.

65. Miyata et al., Angiotensin II receptor blockers and angiotensin converting enzyme inhibitors: implication of radical scavenging and transition metal chelation in inhibition of advanced glycation end product formation. *Arch. Biochem. Biophys.* 419:50-54, 2003.

66. Morcos et al., Activation of tubular epithelial cells in diabetic nephropathy. *Diabetes* 51:3532-3544, 2002.

67. Mowri et al., Glucose enhancement of LDL oxidation is strictly metal ion dependent. *Free Radic. Biol. Med.* 29:814-824, 2000.

68. Mullarkey et al., Free radical generation by early glycation products: a mechanism for accelerated atherogenesis in diabetes. *Biochem. Biophys. Res. Commun.* 173:771-778, 1994.

69. Muntner et al., Plasma lipids and risk of developing renal dysfunction: the atherosclerosis risk in communities study. *Kidney Int.* 58:293-301, 2000.

70. Nagaraj et al., Effects of pyridoxamine on chemical modifications of proteins by carbonyls in diabetic rats: characterization of a major product from the reaction of pyridoxamine with methylglyoxal. *Arch. Biochem. Biophys.* 402: 110-119, 2002.

71. Nourooz-Zadeh et al., Low-density lipoprotein is the major carrier of lipid hydroperoxides in plasma. Relevance to determination of total plasma lipid hydroperoxide concentrations. *Biochem. J.* 313:781-786, 1996.
72. Nangaku et al., Anti-hypertensive agents inhibit in vivo the formation of advanced glycation end products and improve renal damage in a type 2 diabetic nephropathy rat model. *J. Am. Soc. Nephrol.* 14:1212-1222, 2003.
73. Oda and Keane, Recent advances in statins and the kidney. *Kidney Int. Suppl.* 71:S2-S5, 1999.
74. O'Donnell et al., Lovastatin retards the progression of established glomerular disease in obese Zucker rats. *Am. J. Kidney Dis.* 22:83-89, 1993.
75. Park L, et al. 1998. Suppression of accelerated diabetic atherosclerosis by the soluble receptor for advanced glycation end products. Nat. Med. 4: 1025-1031.
76. Price et al., Chelating activity of advanced glycation end-products inhibitors. *J. Biol. Chem.* 276:48967-48972, 2001.
78. Rahbar et al., Novel inhibitors of glycation end products. *Biochem. Biophys. Res. Commun.* 262:651-656, 1999.
79. Rahbar et al., Novel inhibitors of advanced glycation end products (Part II). *Mol. Cell. Biol. Res. Comm.* 3:360-366, 2000.
80. Rahbar and Figarola, Inhibitors and breakers of advanced glycation end products (AGEs): a review. *Curr. Med. Chem.—Immunol. Endocr. Metabol.* Agents 2:135-161, 2002.
81. Rahbar and Figarola, Inhibitors and breakers of advanced glycation end products. *Curr. Med. Chem.—Immunol. Endocrin. Metabol.* 2: 174-186, 2002.
82. Rahbar and Figarola, Novel inhibitors of advanced glycation end products. *Arch. Biochem. Biophys.* 419:63-79, 2003.
83. Ramasamy R, Vannucci S J, Yan S S, et al. 2005. Advanced glycation end products and RAGE: a common thread in aging, diabetes, neurodegeneration, and inflammation. Glycobiology. 15:16R-28R.
84. Requena et al., Lipoxidation products as biomarkers of oxidative damage to proteins during lipid peroxidation reactions. *Nephrol. Dial. Transplant.* 11 (Suppl 5):48-53, 1996.
85. Requena et al., Carboxymethylethanolamine: a biomarker of phospholipid modification during the Maillard reaction in vivo. *J. Biol. Chem.* 272:17473-14779, 1997.
86. Rojas A, Morales M A. 2004. Advanced glycation and endothelial functions: a link towards vascular complications in diabetes. Life Sci. 76: 715-730.
87. Rosca M G, Mustata T G, Kinter M T, et al. 2005. Glycation of mitochondrial proteins from diabetic rat kidney is associated with excess superoxide formation. Am J Physiol Renal Physiol. 289: F420-F430.
88. Rong L L, Trojaborg W, Qu W, et al. 2004. Antagonism of RAGE suppresses peripheral nerve regeneration. FASEB J. 18:11812-11817.
89. Rueckschloss U, Galle J, Holtz J, et al. 2001. Induction of NAD(P)H oxidase by oxidized low-density lipoprotein in human endothelial cells: antioxidative potential of hydroxymethylglutaryl coenzyme A reductase inhibitor therapy. Circulation 104: 1767-1772.
90. Sakata et al., Glycoxidation and lipid peroxidation of low-density lipoprotein can synergistically enhance atherogenesis. *Cardiovasc. Res.* 49:466-475, 2001.
91. Satoh, Serum lipid peroxide in cerebrovascular disorders determined by a new colorimetric method. *Clin. Chim. Acta* 90:37-43, 1978.
92. Schmidt A M, Hori O, Brett J, et al. 1994. Cellular receptors for advanced glycation end products: implications for induction of oxidant stress and cellular dysfunction in the pathogenesis of vascular lesions. Arterioscler Thromb 14: 1521-1528.
93. Schmidt A M, Yan S D, Yan S F, Stern D M. 2000. The biology of the receptor for advanced glycation end products and its ligands. Biochim. Biophys. 1498:99-111.
94. Shanmugam N, Reddy M A, Guha M, Natarajan R. 2003. High glucose-induced expression of proinflammatory cytokine and chemokine genes in monocytic cells. Diabetes 52:1256-1264.
95. Shanmugam N, Kim Y S, Lanting L, Natarajan R. 2003. Regulation of cyclooxygenase-2 expression in monocytes by ligation of the receptor for advanced glycation end products. *J Biol Chem.* 278: 34834-34844.
96. Shaw et al., N-epsilon-(carboxymethyl)lysine (CML) as a biomarker of oxidative stress in long-lived tissue proteins. *Methods Mol. Biol.* 186:129-137, 2002.
97. Singh et al., Advanced glycation end-products: a review. *Diabetologia* 44:129-146, 2001.
98. Slatter et al., The importance of lipid-derived malondialdehyde in diabetes mellitus. *Diabetologia* 43:550-557, 2000.
99. Smith et al., Stimulation of lipid peroxidation and hydroxyl-radical generation by the contents of human atherosclerotic lesions. *Biochem. J.* 286:901-905, 1992.
100. Stadler et al., Direct detection and quanification of transition metal ions in human atherosclerotic plaques: evidence for the presence of elevated levels of iron and copper. *Arterioscler. Thromb. Vasc. Biol.* 24:949-954, 2004.
101. Stefek et al., p-Dimethyl aminobenzaldehyde-reactive substances in tail tendon collagen of streptozotocin-diabetic rats: temporal relation to biomechanical properties and advanced glycation end product (AGE)-related fluorescence. *Biochim. Biophys. Acta* 1502:398-404, 2000.
102. Stith et al., Advanced glycation end products and diabetic complications. *Expert Opin. Invest. Drugs* 11:1205-1223, 2002.
103. Teuscher et al., Nephropathy subsequent to hyperlipidemia. *Clin. Nephrol.* 54:64-67, 2000.
104. Thornalley et al., Formation of glyoxal, methylglyoxal and 3-deoxyglucosone in the glycation of proteins by glucose. *Biochem. J.* 344:109-116, 1999.
105. Thornalley et al., Kinetics and mechanism of the reaction of aminoguanidine with the alpha-oxoaldehydes glyoxal, methylglyoxal, and 3-deoxyglucosone under physiological conditions. *Biochem. Pharmacol.* 60:55-65, 2000.
106. Thorpe and Baynes, Role of oxidative stress in development of complications in diabetes: a new perspective on an old paradigm. *Diabetes* 48:1-9, 1999.
107. Thorpe and Baynes, Maillard reaction products in tissue proteins: new products and new perspectives. *Amino Acids* 25:275-281, 2002.
108. Thuraisingham et al., Increased nitrotyrosine staining in kidneys from patients with diabetic nephropathy. *Kidney Int.* 57:968-972, 2000.
109. Uchida et al., Protein modification by lipid peroxidation products: formation of malondialdehyde-derived N(epsilon)-(2-propenol)lysine in proteins. *Arch. Biochem. Biophys.* 346:45-52, 1997.
110. Ukeda et al., Spectrophotometric assay of superoxide anion formed in Maillard reaction based on highly water-soluble tetrazolium salt. *Anal. Sci.* 18:1151-1154, 2002.
111. Ulrich and Cerami, Protein glycation, diabetes & aging. *Recent Prog. Horm. Res.* 56:1-21, 2001.

112. Vlassara et al., Advanced glycation end-products induce glomerular sclerosis and albuminuria in normal rats. *Proc. Natl. Acad. Sci. USA* 91:11704-11708, 1994.
113. Vlassara, The AGE-receptor in the pathogenesis of diabetic complications. *Diabetes Metab. Res. Rev.* 17:436-443, 2001.
114. Vlassara and Palace, Diabetes and advanced glycation end products. *J. Intern. Med.* 251:87-101, 2002.
115. Voziyan et al., A post-Amadori inhibitor pyridoxamine also inhibits chemical modification of proteins by scavenging carbonyl intermediates of carbohydrate and lipid degradation. *J. Biol. Chem.* 277:3397-3403, 2002.
116. Voziyan et al., Modification of proteins In vitro by physiological levels of glucose: Pyridoxamine inhibits conversion of amadori intermediate to advanced glycation endproducts through binding of redox metal ions. *J. Biol. Chem.* 2003 Sep. 15 [Epub ahead of print].
117. Wautier et al., Activation of NADPH oxidase by AGE links oxidant stress to altered gene expression via RAGE. *Am. J. Physiol. Endocrinol. Metab.* 280:E685-E694, 2001.
118. Wautier J L, Schmidt A M. 2004. Protein glycation: a firm link to endothelial cell dysfunction. Circ Res. 95:233-238.
119. Wendt et al., RAGE drives the development of glomerulosclerosis and implicates podocyte activation in the pathogenesis of diabetic nephropathy. *Am. J. Pathol.* 162:1123-1137, 2003.
120. Wilkinson-Berka et al., ALT-946 and aminoguanidine, inhibitors of advanced glycation, improve severe nephropathy in the diabetic transgenic (mREN-2) 27 rat. *Diabetes* 51:3283-3289, 2002.
121. Wolff, Diabetes mellitus and free radicals. Free radicals, transistion metals and oxidative stress in the aetiology of diabetes mellitus and complications. *Br. Med. Bull.* 49:642-652, 1993.
122. Yamamoto Y, Kato I, Doi T, et al. 2001. Development and prevention of advanced diabetic nephropathy in RAGE-overexpressing mice. J Clin Invest. 108: 261-268.
123. Yan et al., Glycation, inflammation, and RAGE: a scaffold for the macrovascular complications of diabetes and beyond. *Circ. Res.* 93:1159-1169.
124. Yang et al., AGE-breakers cleave model compounds, but do not break Maillard crosslinks in skin and tail collagen from diabetic rats. *Arch. Biochem. Biophys.* 412:42-46, 2003.
125. Zheng et al., Prevention of diabetic nephropathy in mice by a diet low in glycoxidation products. *Diabetes Metab. Res. Rev.* 18:224-237, 2002.

EXAMPLES

Example 1

Treatment of Diabetic and Control Rats

Animal studies were carried out in compliance with policies outlined in "The Guide for the care and Handling of Laboratory Animals" (NIH Publication No. 85-23), which have been approved by the City of Hope National Medical Center Animal Care Committee. Induction of diabetes by STZ and all other procedures were according to the previously published article on LR-90 (25), except that in the present study the diabetic rats under treatment were randomized in 5 groups of ten each: one diabetic control group (0 mg/L), one group receiving 2.5 mg/L, one group receiving 10 mg/L, a third group receiving 20 mg/L and a fourth group receiving 50 mg/L of LR-90 in drinking water (FIG. 1). Both plasma glucose and body weight were checked before administration of the drug, and no differences were detected among the two non-diabetic groups and five diabetic treatment groups. All animals were housed individually and were given free access to food (Purina rodent chow 5001, Ralston Purina, Richmond, Ind., USA) and water. Glycemic control and body weights were monitored periodically. In order to limit hyperglycemia and ensure that animals maintained body weight, diabetic animals received 3 IU of ultralente insulin (Humulin U, Eli Lilly, Indianapolis, Ind., USA) two to three times per week. The study was carried out over 32 weeks.

Blood (from the tail vein) and urine samples were collected from rats for glycemic control analysis and albuminuria measurements. Plasma glucose was measured using a glucose analyzer machine (YSI 2300 STAT, Yellowsprings, Ohio, USA). HbAlc concentration was measured by HPLC (Bio-Rad DIAMAT, Hercules, Calif., USA). Total plasma triglycerides and cholesterol concentrations were quantified at the end of the study using the Vitros 250 Chemistry System (Johnson & Johnson, Rochester, N.Y., USA). Progression of renal dysfunction was assessed by measuring urinary albumin-to-creatinine ratio (ACR). Rats were housed in metabolic cages (Nalge, Rochester, N.Y., USA) for 24 hr and urine was collected in a collection beaker with several drops of toluene to inhibit microbial growth. Urinary albumin and creatinine concentrations were quantified immunologically using the Nephrat/Creatinine Companion kits (Exocell), and the ACR value was calculated for each rat.

At the end of study, the rats were weighed and anaesthetized with isofluorane and blood was drawn by heart puncture and transferred into heparinized and non-heparinized vacutainer tubes on ice. These blood samples were later centifuged for plasma and serum collection respectively, and stored at −70° C. until the time of analysis. Rats were killed by over-anesthetization and cardiac puncture and the kidneys were removed immediately, weighed, decapsulated and rinsed in PBS buffer. Sections of the kidneys were stored in 10% NBF for subsequent microscopic examinations and immunohistochemistry.

Figure 2:
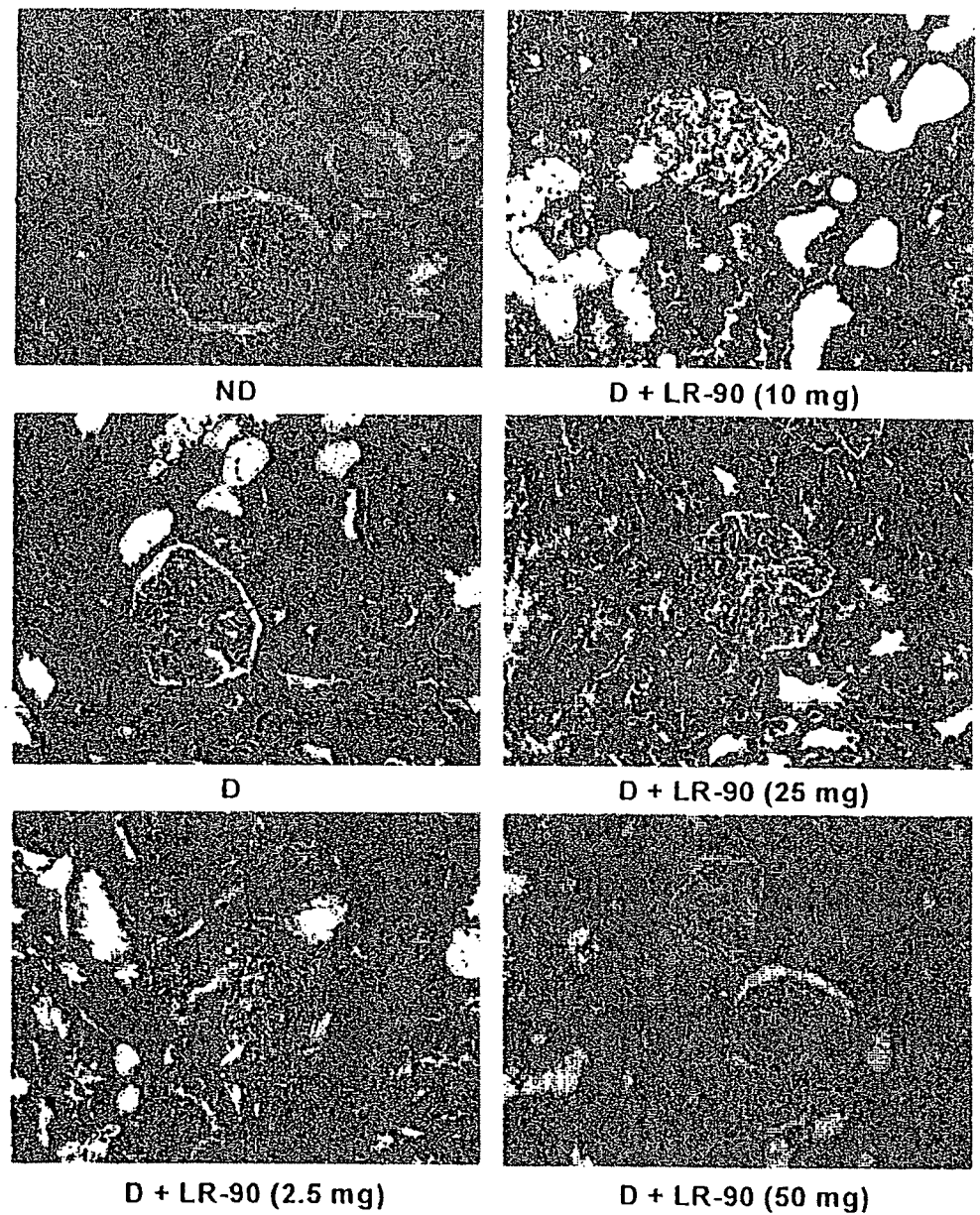
FIG. 2: Trichrome staining of kidneys sections—Effects of various concentrations of LR-90 on collagen deposition and tubular degeneration.

Diabetes was associated with increased ACR (P<0.001 vs. non-diabetic control, Table 2). Additionally, kidneys of diabetic animals showed severe mesangial expansion and glomerulosclerosis as evidenced by increased accumulation of PAS-positive materials in the mesangial area of the glomeruli (data not shown) and increased collagen deposition and tubular degeneration in the glomeruli as revealed by Trichrome staining (FIG. 2). Treatment of diabetic rats with LR-90 inhibited the rise in ACR in almost dose-dependent manner, with 25 and 50 mg/L doses showing statistically significant differences with untreated diabetic animals (Table 2). Additionally, LR-90 treatment reduced the levels of PAS-positive materials and prevented collagen deposition and tubular degeneration in the kidney glomeruli (FIG. 2), with 25 and 50 mg/L concentrations showing contrastingly marked difference compared with untreated diabetic kidneys.

Diabetic animals significantly weighed less than non-diabetic rats (Table 2). LR-90-treated diabetic and non-diabetic rats showed slight increase in weight compared with their untreated counterparts, but the difference was not statistically significant. Diabetic rats also had significantly increased plasma glucose and HbAlc concentrations compared with the non-diabetic rats (P<0.001, Table 2). Treatment of diabetic rats with various doses of LR-90 had no affect on both plasma glucose and HbAlc concentrations.

Statistical analyses were performed using Prism software (GraphPad, San Diego, Calif., USA). Unless otherwise indicated, data are presented as Means±Std. Group comparisons were analyzed using one-way ANOVA and subsequent post-hoc analysis by Tukey's test. A P value of less than 0.05 was considered statistically significant.

TABLE II

Effects of various concentrations of LR-90 on body weight and metabolic parameters in STZ-diabetic rats.

| Group | n | Body wt. (g) | Plasma Glucose (mmol/l) | HbA1c (%) | ACR (mg/mg) |
|---|---|---|---|---|---|
| ND | 6 | 645.2 ± 65.5 | 8.9 ± 1.7 | 1.2 ± 0.1 | 0.41 ± 0.24 |
| ND + LR-90(50) | 6 | 698.5 ± 93.4 | 8.9 ± 1.0 | 1.2 ± 0.1 | 0.42 ± 0.32 |
| D | 3 | 294.0 ± 65.6* | 29.8 ± 5.6* | 2.8 ± 0.5* | 3.42 ± 1.79* |
| D + LR-90(2.5) | 4 | 305.8 ± 52.1* | 29.9 ± 5.9* | 2.6 ± 0.6* | 2.35 ± 1.96* |
| D + LR-90(10) | 5 | 306.8 ± 71.4* | 30.8 ± 2.9* | 3.0 ± 0.4* | 2.60 ± 1.74* |
| D + LR-90(25) | 6 | 312.0 ± 71.9* | 26.7 ± 2.4* | 2.9 ± 0.4* | 1.75 ± 1.43** |
| D + LR-90(50) | 8 | 326.4 ± 62.3* | 31.6 ± 3.9* | 3.0 ± 0.2* | 1.39 ± 1.17** |

*P < 0.01 vs. non-diabetic control rats;
**p < 0.05 vs. diabetic rats.
Numbers in parentheses indicate drug dosages (mg/per liter drinking water daily).
a ND = non-diabetic; D = diabetic
b p < 0.05 vs. non-diabetic control rats
c p < 0.05 vs. diabetic rats Example 2

Effects on Dyslipidemia

Figure 3:
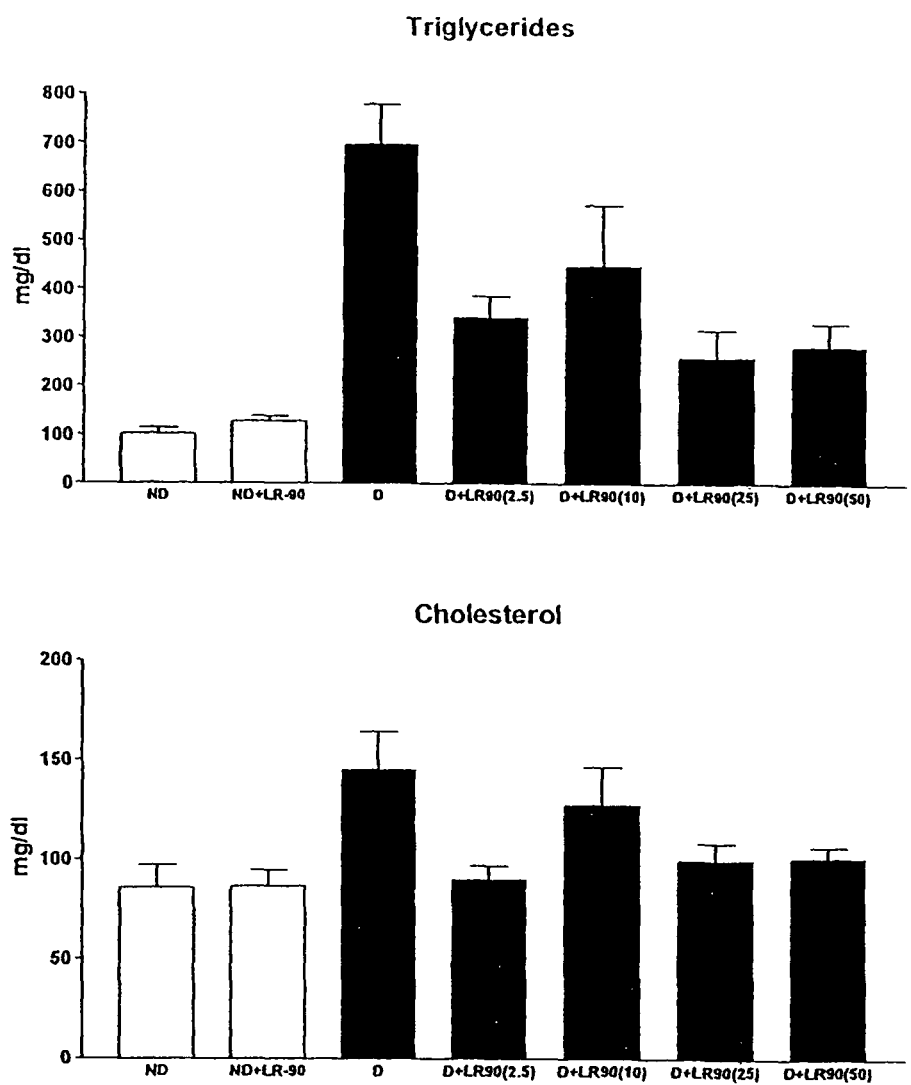
FIG. 3: Effect of various concentrations of LR-90 on plasma lipids.

Diabetic rats showed elevated levels of plasma lipids compared with non-diabetic rats (FIG. 3). Plasma triglycerides increased to 598±110 mg/dL in diabetic rats compared to 86±14 mg/dL in untreated non-diabetic controls (P<0.001). Plasma cholesterol concentrations showed a similar increase in diabetic animals (85±11 mg/dL in non-diabetic vs. 145±19 mg/dL in diabetic rats) (P<0.001). LR-90 had no effect on lipid metabolism in non-diabetic animals. However, diabetic rats treated with LR-90 showed significant reduction in both triglyceride and cholesterol concentrations. As much as 50% reduction in triglyceride concentration was observed even at the lowest concentration (25 mg/L) tested, and both 25 and 50 mg/L treatments showed [3] 60% reduction. As for the cholesterol lowering effects, with the exception of 10 mg/L treatment, all concentrations tested nearly normalized the cholesterol concentration to that of non-diabetic animals (FIG. 3).

Example 3

AGE Immunohistochemistry

Figure 4:
FIG. 4: Effects of various concentrations of LR-90 on renal CML-AGE accumulation.
Figure 4:
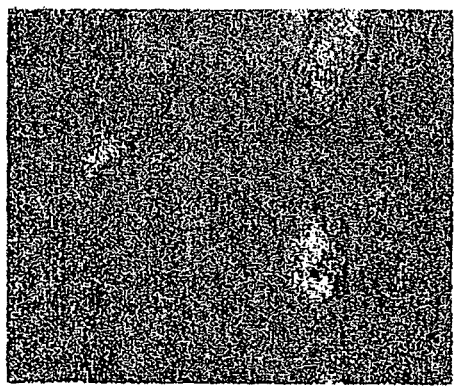
Figure 4:
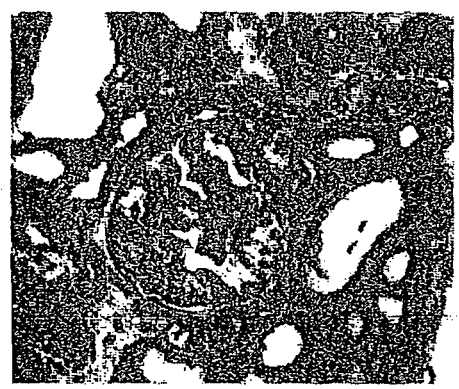
Figure 4:
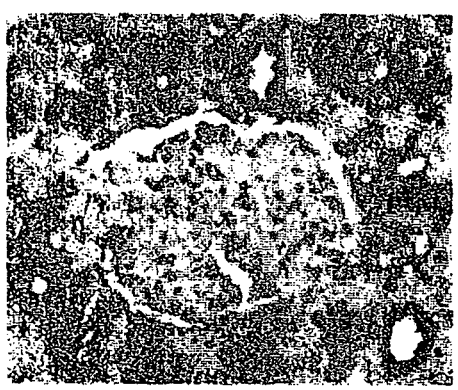
Figure 4:
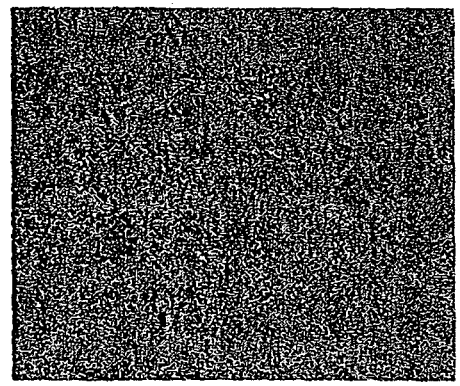
Figure 4:
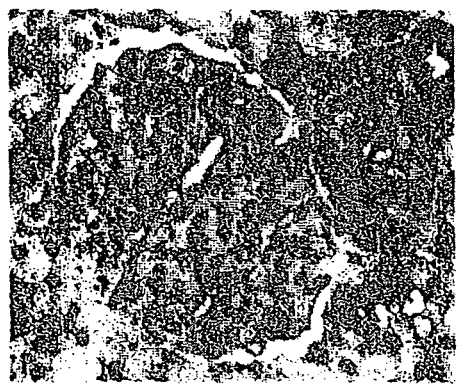
Figure 5:
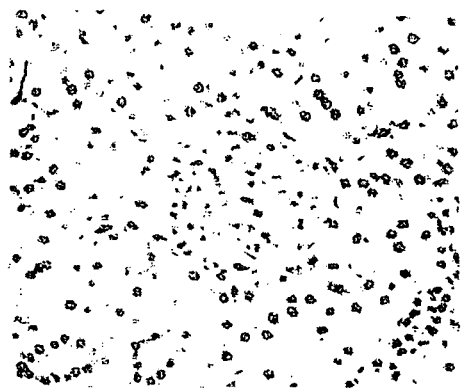
FIG. 5: Effects of various concentrations of LR-90 on renal RAGE protein expression.
Figure 5:
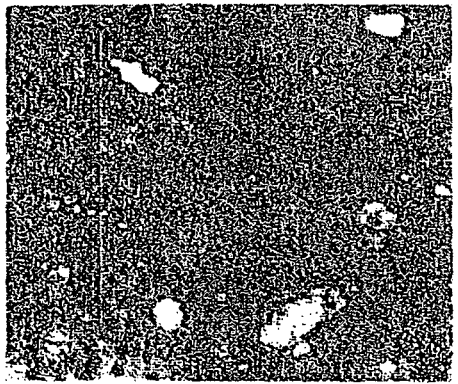
Figure 5:
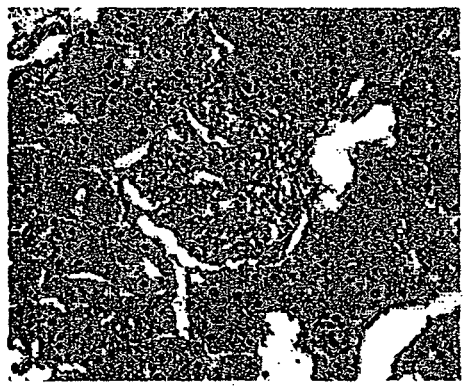
Figure 5:
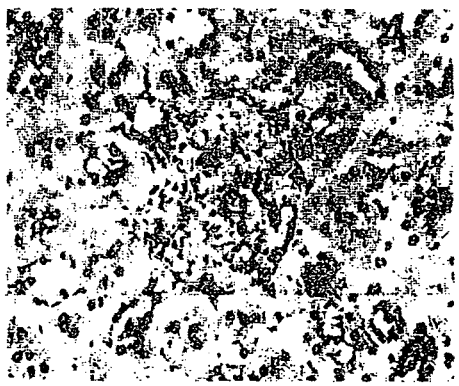
Figure 5:
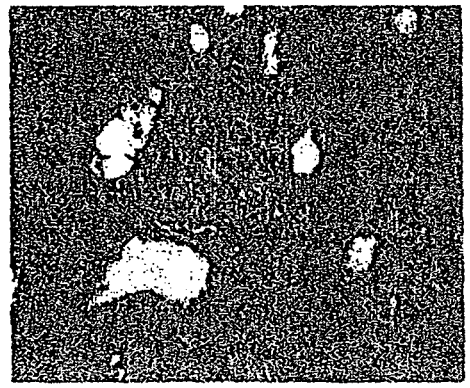
Figure 5:
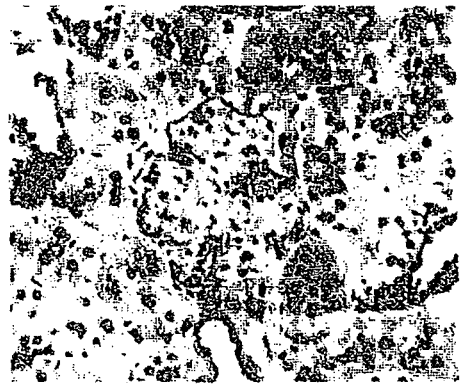

Formalin-fixed parafilm embedded kidney sections (2 mm thick) were mounted on slides and stained with 6D12 monoclonal anti-CML-AGE, polyclonal rabbit anti-RAGE and polyclonal goat anti-nitrotyrosine antibodies as described before (25). Immunohistochemical staining for AGEs in rat kidney demonstrated that there was widespread staining for these markers in the kidney glomeruli and cortical tubules in diabetic rats compared with the non-diabetic control rats (FIG. 4). Similarly, RAGE protein expression in the glomeruli was visibly higher in diabetic rats compared with non-diabetic animals (FIG. 5). Treatment with increasing concentrations of LR-90 visibly reduced the CML-AGE and RAGE protein expression accumulation in these regions (FIGS. 4 and 5), with both 25 and 50 mg/L treatments again showing the best inhibitory effects.

Example 4

Effect on S100b-Induced THP-1 Cells

Human THP-1 monocytic cells were obtained from the American Type Culture Collection and cultured as described (27) in RPMI 1640 medium supplemented with 10% fetal calf serum (FCS), glutamine, HEPES, streptomycin/penicillin (100 mg/ml/100 units/ml), 50 uM-mercaptoethanol, and 5.5 mM D-glucose in a 5% CO2 incubator at 37° C. THP-1 cells ($5 \times 10^5$ cells/ml) in 4 ml of medium were pre-treated with various concentrations of LR-90 (0, 25, 50, 100 and 200 ug/ml; prepared in 20 mM stock solution in DMSO) for 1 hr. Control cells received DMSO vehicle only. Thereafter, S100b (20 mg/ml) was added and cells re-incubated for 4 hr. The cell suspension was then centrifuged at 200 g, the supernatant was removed and the cell pellet was frozen at −70° C. for subsequent RNA extraction.

Cell Viability Test—THP-1 cells were seeded onto 6-well plates at a concentration of $\sim 5 \times 10^5$/ml in RPMI medium containing 10% FCS as above, and then incubated with various concentrations of LR-90 or control medium alone for 24 hr at 37° C., 5% $CO_2$. After incubation, overall cell counts were measured using a cell counter (Coulter Z1 Cell and Particle Counter, Beckman Coulter Inc., Fullerton, Calif.), and the number of viable cells determined by hemocytometer counts of Trypan Blue—impermeable cells.

RNA Extraction and Relative RT-PCR-Total RNA was isolated by the RNA-STAT-60 reagent method (Teltest, Friendswood, Tex.), and 1 mg was used for the RT reaction using a Gene Amp RNA PCR kit. A total cDNA corresponding to 0.05 mg of RNA was then used in multiplex PCR reactions containing gene-specific primers (Table 1) paired with Quantum RNA 18S internal standards, and the multiplex PCR reactions were performed for 30-44 cycles in a Gene-Amp 9700 machine (Applied Biosystems Inc., Foster City, Calif., USA). PCR products were fractionated on 2.5% agarose gels, photographed using Alpha Imager 2000, and analyzed with Quantity 1 software (Bio-Rad Laboratories, Hercules, Calif.). Results were expressed as fold stimulation over control after normalizing with paired 18S RNA gene.

TABLE 1

Primer sequences and PCR conditions.

| Target Gene | PCR Primer Sequence | PCR Protocol | PCR product (bp) | |
|---|---|---|---|---|
| MCP-1 | F: 5'-GCCTTAAGTAATGTTAATTCTTAT-3'<br>R: 5'-GGTGTAATAGTTACAAAATATTCA-3' | 95° C./30 s<br>57° C./30 s (28)<br>72° C./30 s<br>33 cycles | 239 | [SEQ ID NO: 1]<br>[SEQ ID NO: 2] |
| RAGE | F: 5'-AAGCCCCTGGTGCCTAATGAG-3'<br>R: 5'-CACCAATTGGACCTCCTCCA-3' | 95° C./30 s<br>59° C./30 s (29)<br>72° C./30 s<br>30 cycles | 239 | [SEQ ID NO: 3]<br>[SEQ ID NO: 4] |
| COX-2 | F: 5'-ATCTACCCTCCTCAAGTCCC-3'<br>R: 5'-TACCAGAAGGGCAGGATACAG-3' | 95° C./30 s<br>64° C./30 s (30)<br>72° C./30 s<br>33 cycles | 708 | [SEQ ID NO: 5]<br>[SEQ ID NO: 6] |
| NADPH Oxidase* | F: 5'-CAACAAGAGTTCGAAGACAA-3'<br>R: 5'-CCCCTTCTTCTTCATCTGTA-3' | 95° C./30 s<br>59° C./30 s (31)<br>72° C./30 s<br>44 cycles | 687 | [SEQ ID NO: 7]<br>[SEQ ID NO: 8] |
| IP-10 | F: 5'-TGAAAAAGAAGGGTGAGAAGAG-3'<br>R: 5'-GGAAGATGGGAAAGGTGAGG-3' | 95° C./30 s<br>59° C./30 s (27)<br>72° C./30 s<br>33 cycles | 413 | [SEQ ID NO: 9]<br>[SEQ ID NO: 10] |

*$gp91^{phox}$ subunit.

Measurement of MCP-1 levels by ELISA. Supernatants of THP-1 cells ($5 \times 10^5$ cells/ml) cultured in RPMI 1640 medium containing 2% FBS for 18 hrs under control or LR-90 treated conditions were used to assay secreted MCP-1 levels using the Quantikine ELISA kit. Medium alone without cells was incubated under the same conditions and used as blank control for the ELISA.

Data Analyses. Statistical analyses were performed using Prism software (GraphPad, San Diego, Calif., USA). Unless otherwise indicated, data are presented as Means±Std. Group comparisons were analyzed using one-way ANOVA and subsequent post-hoc analysis by Tukey's test. A P value of less than 0.05 was considered statistically significant.

Previous results indicate that S100b treatment upregulated the expression of several groups of genes, including adhesion molecules, chemokines and their receptors and other signaling molecules and enzymes. We selected several of these pro-inflammatory mediators that have been known to be involved in diabetic atherosclerosis and oxidative stress, and test if LR-90 can suppress or downregulate the expression of these genes. THP-1 cells incubated with S100b for 4 hours showed increased mRNA expression of RAGE, a known S100b ligand (FIG. 6). Similarly, we also observed marked upregulation of the chemokine MCP-1 (FIG. 7), as well as the inflammatory COX-2 enzyme (FIG. 8) and the redox-sensitive NADPH oxidase enzyme (FIG. 9). On the other hand, THP-1 monocytes pre-treated with LR-90 1 hr before S100b incubation profoundly suppressed the expression of all these genes in a concentration-dependent manner, with the highest concentrations tested (100 and 200 ug/ml) exhibiting statistically significant reduction in mRNA expression of the genes analyzed. Interestingly, LR-90 treatment also inhibited MCP-1 protein expression in a concentration-dependent manner (FIG. 7, lower panel).

To confirm that LR-90 indeed suppressed mRNA production of these inflammatory genes by blocking key signaling and/or activation pathways and not by apoptosis or cell toxicity, we exposed THP-1 cells to the same concentrations of LR-90 used in the S100b experiments and incubated the cells for 24 hr. Cell counts after incubation were normal and statistically similar to the untreated cells (FIG. 10, upper panel). Furthermore, Trypan blue staining indicates the LR-90 treated cells were viable (FIG. 10, lower panel).

The invention claimed is:

1. A method of inhibiting AGE receptor (RAGE) expression in a mammal in need thereof, comprising administering a RAGE expression inhibiting effective amount of methylene bis 4,4'-(2-chlorophenylureidophenoxyisobutyric acid) or its pharmaceutically acceptable salt or ester to said mammal.

* * * * *